US006802806B2

(12) United States Patent
McCarthy et al.

(10) Patent No.: US 6,802,806 B2
(45) Date of Patent: Oct. 12, 2004

(54) APPARATUS FOR USE WITH AN INFLOW CANNULA OF VENTRICULAR ASSIST DEVICE

(75) Inventors: Patrick M. McCarthy, Hunting Valley, OH (US); Ji-Feng Chen, Lakewood, OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 53 days.

(21) Appl. No.: 10/252,454

(22) Filed: Sep. 23, 2002

(65) Prior Publication Data

US 2004/0059178 A1 Mar. 25, 2004

(51) Int. Cl.[7] ................................................ A61M 1/10
(52) U.S. Cl. ........................................................ 600/16
(58) Field of Search ............................. 600/16, 17, 18; 623/3.1, 3.21, 3.25, 3.26

(56) References Cited

U.S. PATENT DOCUMENTS

| | | | | |
|---|---|---|---|---|
| 4,003,382 A | | 1/1977 | Dyke | |
| 4,133,303 A | | 1/1979 | Patel | |
| 4,564,014 A | | 1/1986 | Fogarty et al. | |
| 4,650,486 A | * | 3/1987 | Chareire | 623/3.26 |
| 4,955,856 A | | 9/1990 | Phillips | |
| 5,242,418 A | | 9/1993 | Weinstein | |
| 5,334,153 A | | 8/1994 | McIntyre et al. | |
| 5,360,401 A | | 11/1994 | Turnland | |
| 5,391,172 A | | 2/1995 | Williams et al. | |
| 5,425,714 A | | 6/1995 | Johnson et al. | |
| 5,445,646 A | | 8/1995 | Euteneuer et al. | |
| 5,458,615 A | | 10/1995 | Klemm et al. | |
| 5,571,135 A | | 11/1996 | Fraser et al. | |
| 5,578,009 A | | 11/1996 | Kraus et al. | |
| 5,591,138 A | | 1/1997 | Vaillancourt | |
| 5,653,684 A | | 8/1997 | Laptewicz et al. | |
| 5,674,192 A | | 10/1997 | Sahatjian et al. | |
| 5,685,865 A | | 11/1997 | Cosgrove et al. | |
| 5,695,469 A | | 12/1997 | Segal | |
| 5,755,708 A | | 5/1998 | Segal | |
| 5,861,010 A | | 1/1999 | Boussignac et al. | |
| 5,882,334 A | | 3/1999 | Sepetka et al. | |
| 5,911,728 A | | 6/1999 | Sepetka et al. | |
| 6,001,056 A | | 12/1999 | Jassawalla et al. | |
| 6,007,478 A | | 12/1999 | Siess et al. | |
| 6,123,725 A | * | 9/2000 | Aboul-Hosn | 623/3.25 |
| 6,123,726 A | * | 9/2000 | Mori et al. | 623/3.27 |
| 6,186,999 B1 | | 2/2001 | Chen | |
| 6,217,548 B1 | | 4/2001 | Tsugita et al. | |
| 6,217,568 B1 | | 4/2001 | Jepson et al. | |

OTHER PUBLICATIONS

D. Farrar et al., Effectiveness of Design Improvements and Patient Management to Reduce Mechanical Malfunctions and Infections with the Heartmate Ve Lvas Rematch Clinical Trial.

(List continued on next page.)

*Primary Examiner*—George Manuel
(74) *Attorney, Agent, or Firm*—Tarolli, Sundheim, Covell & Tummino L.L.P.

(57) ABSTRACT

An apparatus (10) for use with an inflow cannula (12) of a ventricular assist device (VAD) (14). The cannula (12) has a first part (30) for connecting with a ventricle (22) of a heart (24) and a second part (32) for connecting with the VAD (14). The apparatus (10) comprises a flexible conduit (60) having oppositely disposed first and second ends (70 and 72) and a main body portion (68) intermediate the ends. The main body portion (68) is movable between a radially collapsed closed condition in which blood flow through the conduit (60) is blocked and a radially expanded open condition in which blood flow through the conduit is unrestricted. A first connector (64) connects the first end (70) of the conduit (60) to the first part (30) of the inflow cannula (12). A second connector (62 and 66) connects the second end (72) of the conduit (60) to the second part (32) of the inflow cannula (12). Several designs are disclosed for securing the connectors (64, 62, and 66) together to prevent relative movement of the ends (70, 72) away from each other.

52 Claims, 12 Drawing Sheets

OTHER PUBLICATIONS

I.D. Gregoric, et al., A Newley Designed Inflow Valve Conduit for the Thoratec HeartMate XVE (In–vivo Testing) [Poster Astract]. ASAIO Journal: Mar.–Apr. 2003, vol. 49(2).

D. Farrar, et al., "Effectiveness of Design Improvements and Patient Management to Reduce Mechanical Malfunctions and Infections with the HeartMate VE LVAS in the Rematch . . . Clinical Trial.", Heart Failure and Circulatory Support Summit, Cleveland, Aug. 22–25, 2002.

Bartley Griffith, et al., "HeartMate II Left Ventricular Assist System: From Concept to First Clinical Use." The Annals of Thoracic Surgery. Mar. 2001, vol. 71(3) Sup.

H. Loree II, et al., "The HeartMate III: Design and In Vivo Studies of a Maglev Centrifugal Left ventricular Assist Device." Artificial Organs: May 2001, vol. 25(5): 386–91.

G. Schreiner, Inflow System for Long–term Left Ventricular Assist Device (LVAD). ASAIO Transactions: Apr. 1980, vol. 26: 24–28.

R. Hegyeli, et al., Report on Left Ventricular Assist Device. U.S. Department of Health, Education, and Welfare Publication: Jan. 1974.

W. Bernhard, et al., A Temporary Ventricular Assist Device for Patients Exhibiting Intractable Post–Cardiotomy Shock. Assited Circulation 2: 1984.

* cited by examiner

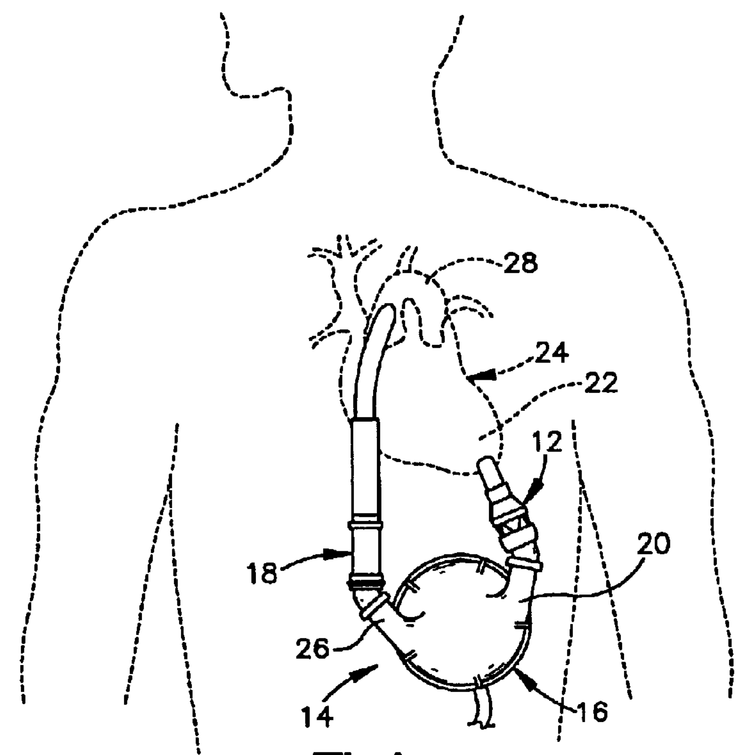
Fig.1
(PRIOR ART)
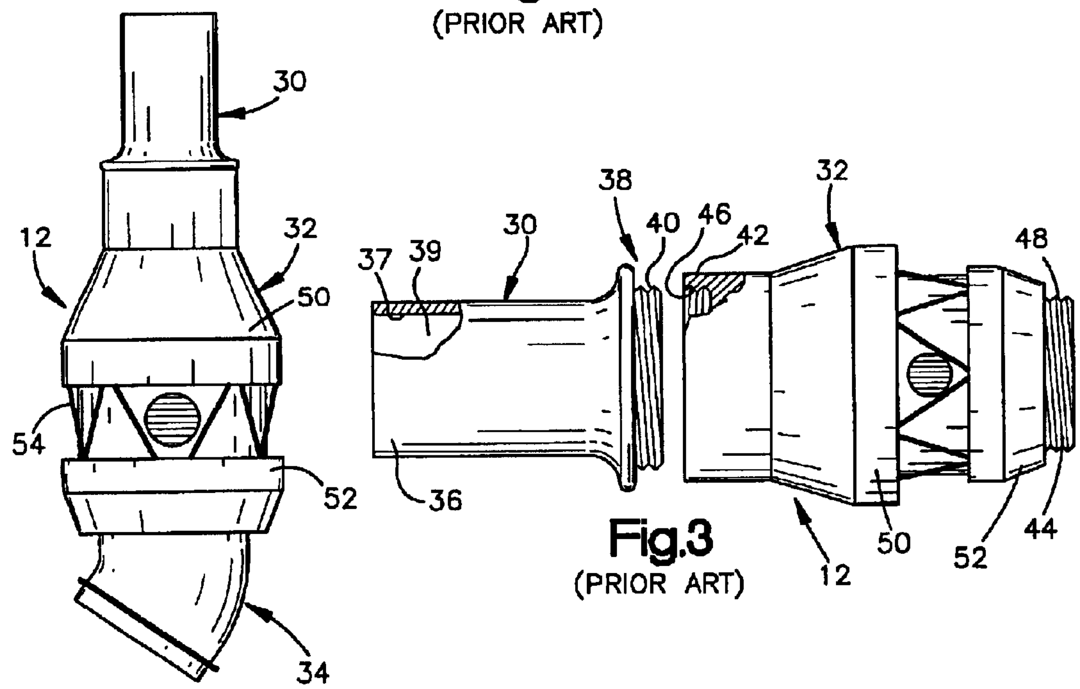
Fig.2
(PRIOR ART)
Fig.3
(PRIOR ART)

34
52
54
50
12
32
42
86
88
62
82
90
66
92
10
78
76
72
60
74
68
70
64
65
40
30

34
52
32
50
12
62
66
6
10
68
60
64
30

80
82
62
88
84
66
86
12
72
10
68
78
60
64
70
30

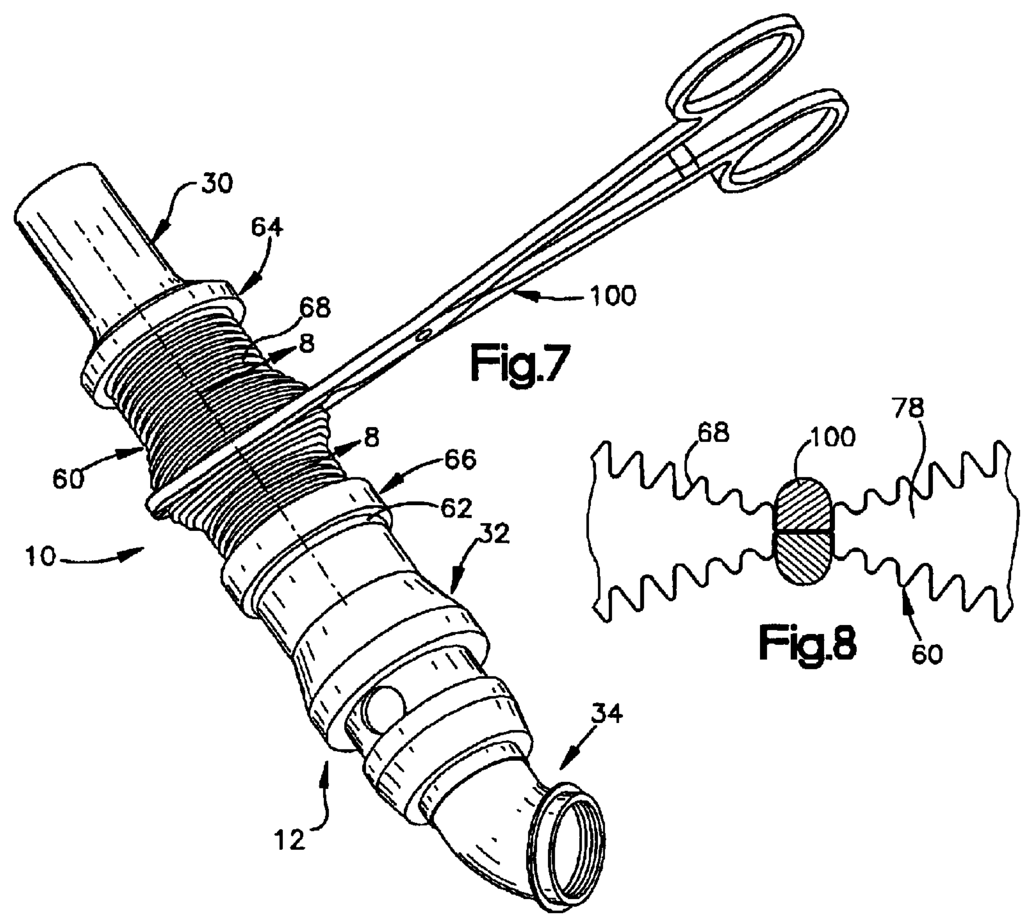
Fig.7
Fig.8
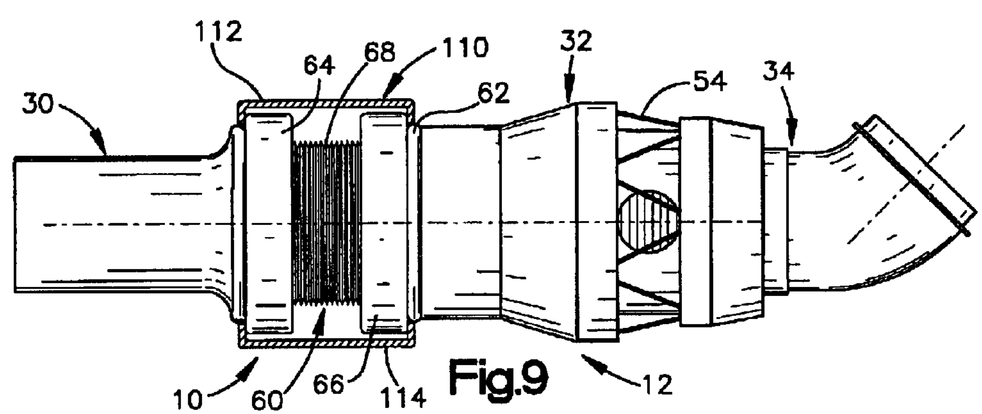
Fig.9

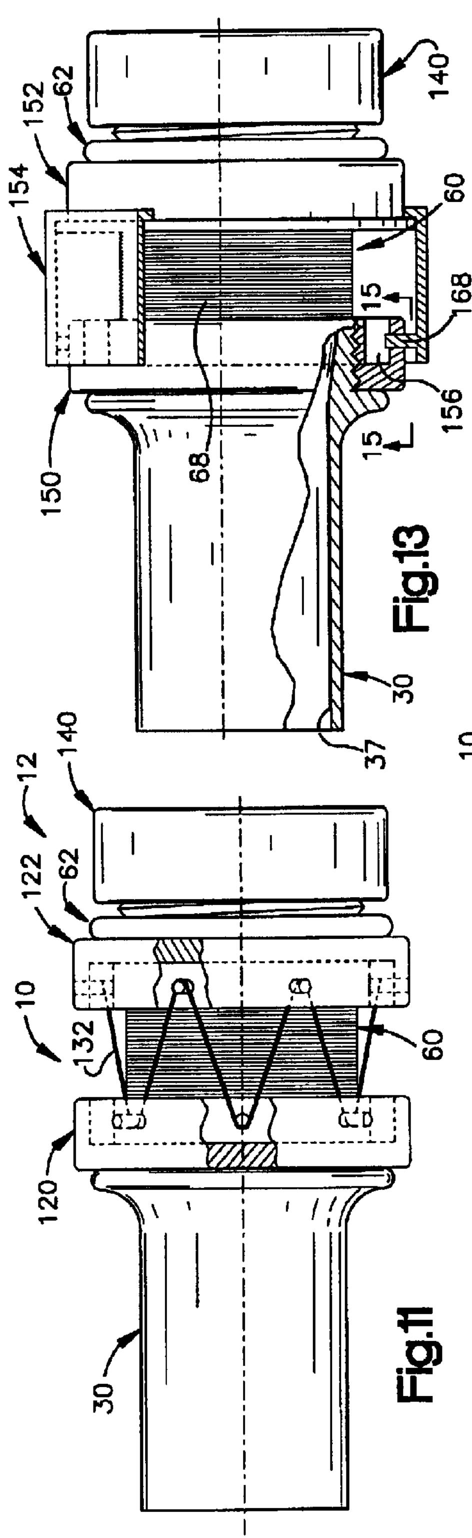
Fig.13
Fig.11
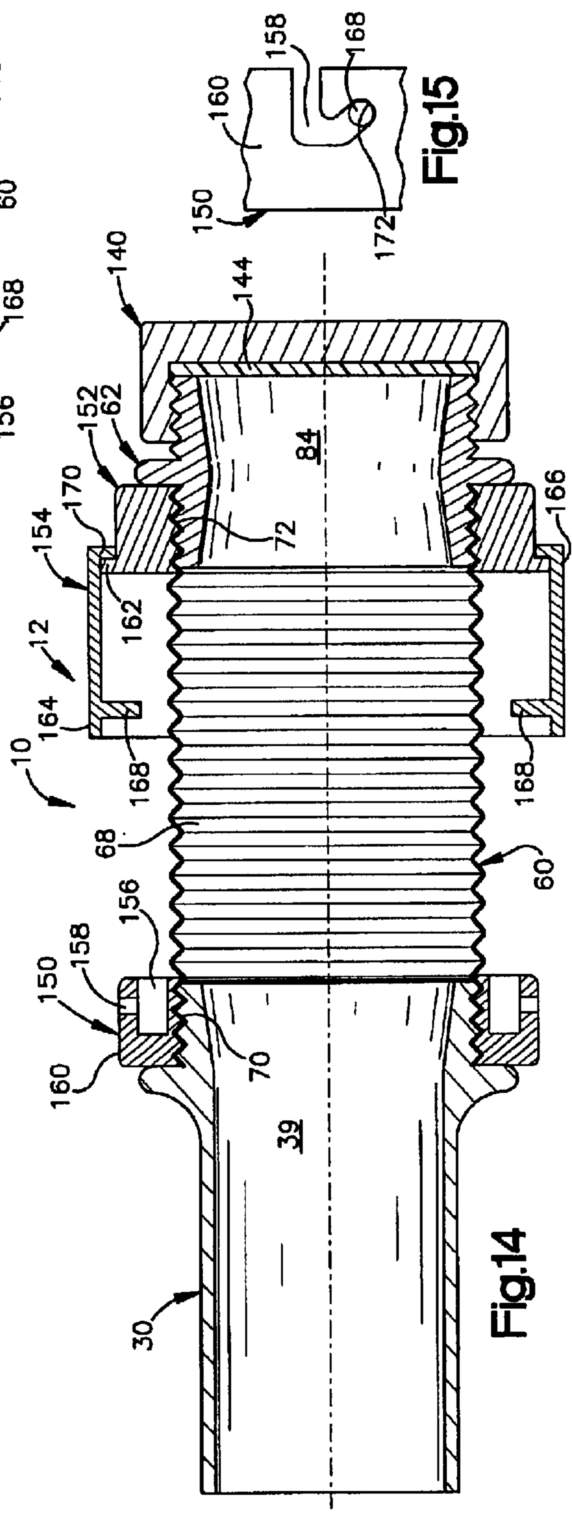
Fig.15
Fig.14

34
12
52
50
32
564
570
510
560
582
568
572
562
38
580
30
36

34
12
52
50
32
572
564
568
510
570
578
576
42
560
38
562
30
36

APPARATUS FOR USE WITH AN INFLOW CANNULA OF VENTRICULAR ASSIST DEVICE

TECHNICAL FIELD

The present invention is directed to an apparatus for use with an inflow cannula of a ventricular assist device.

BACKGROUND OF THE INVENTION

Each year in the United States, about 2000 or so patients with end-stage heart failure receive heart transplants. Unfortunately, there are another 30,000 to 100,000 patients who could benefit from a heart transplant, but who do not receive a donor heart due to, among other things, limited supply.

One alternative that many clinicians are employing to combat the short supply of donor hearts is the temporary implantation of a ventricular assist device (VAD) such as a left ventricular assist (LVA) pump. The LVA pump draws blood from the left ventricle and pumps the blood into the aorta. The LVA pump shares the load on the ventricle, which allows the heart to "rest". While resting with the assistance of the LVA pump, the damaged heart muscle can even start to repair itself. In a few cases, the heart has been able to sufficiently repair itself such that the LVA pump could be removed and the patient no longer needed a transplant. In other cases, the LVA pump stabilizes the patient's condition and, in lieu of a heart transplant, remains implanted, thereby becoming more of a permanent solution than a temporary solution.

For a number of reasons, it is desirable that the inflow cannula, which is the part of a VAD that is fluidly connected to the heart, be occludable so that blood flow through the VAD can be temporarily blocked. For example, the ability to occlude blood flow through the inflow cannula is needed in cases where the VAD has allowed the heart to heal itself and the VAD is to be removed. In such cases, it can also be desirable to be able to close and seal the inflow cannula, but leave it attached to the heart so that the opening in the heart through which the inflow extends does not have to be closed. It is also desirable to be able to temporarily occlude blood flow through the inflow cannula in cases where the VAD is "permanent" because parts of the VAD may need to be serviced or replaced over time.

SUMMARY OF THE INVENTION

The present invention is an apparatus for use with an inflow cannula of a ventricular assist device (VAD). The inflow cannula has a first part for connecting with a ventricle of a heart and a second part for connecting with the VAD. The apparatus comprises a conduit made of a flexible material. The conduit has oppositely disposed first and second ends and a main body portion intermediate the ends. The main body portion of the conduit is movable between a radially collapsed closed condition in which blood flow through the conduit is blocked and a radially expanded open condition in which blood flow through the conduit is not blocked. First connecting means connects the first end of the conduit to the first part of the inflow cannula. Second connecting means connects the second end of the conduit to the second part of the inflow cannula.

According to one aspect of the invention, the main body portion has an accordion-like configuration to allow for relative axial and radial movement of the ends.

According to another aspect of the invention, the first connecting means comprises a first nut for threadedly engaging threads on the first part on the inflow cannula.

According to another aspect of the invention, the second connecting means comprises a second nut and a threaded adapter. The adapter has a first threaded portion for engaging threads on the second part of the inflow cannula and a second threaded portion for threadedly engaging the second nut.

According to another aspect of the invention, the first end of the conduit is sandwiched between threads on the first nut and the threads on the first part of the inflow cannula.

According to another aspect of the invention, the second end of the conduit is sandwiched between threads on the second nut and the second threaded portion on the adapter.

According to another aspect of the invention, the apparatus further comprises means for occluding blood flow through the conduit.

According to another aspect of the invention, the means for occluding blood flow comprises a surgical clamp.

According to another aspect of the invention, the means for occluding blood flow comprises a plug connected to the second connecting means.

According to another aspect of the invention, the apparatus further comprises means for preventing relative axial and radial movement of the ends of the conduit.

According to another aspect of the invention, the means for preventing movement of the ends comprises sutures that extend between the first and second connecting means and secure the first and second connecting means to each other.

According to another aspect of the invention, the first connecting means comprises an adhesive for bonding the first end of said conduit to the first part on the inflow cannula.

According to another aspect of the invention, the second connecting means comprises a rotating seal disposed at the second end of the conduit. The rotating seal is for sealingly engaging the second part of the inflow cannula and for allowing rotation of the second part relative to the rotating seal.

According to another aspect of the invention, the means for preventing movement of the ends comprises a hinged clamshell-style sleeve that encloses the first and second connecting means and holds the main body portion of the conduit in an axially compressed condition.

According to another aspect of the invention, the means for preventing movement of the ends comprises a collar that connects the first and second connecting means to each other.

The present invention also provides an apparatus for use with an inflow cannula of a ventricular assist device (VAD). The inflow cannula has a first part for connecting with a ventricle of a heart and a second part for connecting with the VAD. The apparatus comprises a conduit having oppositely disposed first and second ends and a main body portion intermediate the ends. The main body portion has a resiliently flexible section that is compressible to a closed condition in which blood flow through the conduit is blocked. First connecting means connects the first end of the conduit to the first part of the inflow cannula. Second connecting means connects the second end of the conduit to the second part of the inflow cannula.

The present invention also provides an apparatus for use with an inflow cannula for directing blood flow from a heart to a ventricular assist device (VAD). The inflow cannula has a first part for connecting with a ventricle of the heart and a second part for connecting with the VAD. The apparatus comprises a conduit made of a flexible material. The conduit has oppositely disposed threaded first and second ends and a main body portion intermediate the ends. The main body portion is movable between a radially collapsed closed condition in which blood flow through the conduit is blocked and a radially expanded open condition in which blood flow through the conduit is not blocked. A first nut is circumferentially disposed about the first end of the conduit for connecting the first end to the first part of the inflow cannula. A threaded adapter connects to the second part of the inflow cannula. A second nut is circumferentially disposed about the second end of the conduit and connects the second end to the adapter.

The present invention further provides an apparatus for use with an inflow cannula for directing blood flow from a heart to a ventricular assist device (VAD). The inflow cannula has a first threaded part for connecting with a ventricle of the heart and a second threaded part for connecting with the VAD. The apparatus comprises a conduit having oppositely disposed threaded first and second ends and a main body portion intermediate the ends. The main body portion has a resiliently flexible section that is compressible to a closed condition in which blood flow through the conduit is blocked. A first nut is circumferentially disposed about the first end of the conduit for connecting the first end to the first threaded part of the inflow cannula. A threaded adapter connects to the second threaded part of the inflow cannula. A second nut is circumferentially disposed about the second end of the conduit and connecting the second end to the adapter.

The present invention further provides an apparatus for use with an inflow cannula of a ventricular assist device (VAD). The inflow cannula has a first part for connecting with a ventricle of a heart and a second part for connecting with the VAD. The apparatus comprises a conduit made of a flexible material. The conduit has oppositely disposed first and second ends and a main body portion intermediate the ends. The main body portion has an accordion-like configuration to allow for relative axial and radial movement of the ends. First connecting means connects the first end of the conduit to the first part of the inflow cannula. Second connecting means connects the second end of the conduit to the second part of the inflow cannula. Means for occluding blood flow through the main body portion of the conduit is also included.

The present invention further provides an apparatus for use with an inflow cannula for directing blood flow from a heart to a ventricular assist device (VAD). The inflow cannula has a first part for connecting with a ventricle of a heart and a second part for connecting with the VAD. The apparatus comprises a conduit made of a flexible material. The conduit has oppositely disposed first and second ends and a main body portion intermediate the ends. The main body portion has an accordion-like configuration to allow for relative axial and radial movement of the ends. A first nut is circumferentially disposed about the first end of the conduit for connecting the first end to the first part of the inflow cannula. An adapter connects to the second part of the inflow cannula. A second nut is circumferentially disposed about the second end of the conduit and connects the second end to the adapter. Means for occluding blood flow through the main body portion of the conduit is also included.

In accordance with another embodiment, the present invention also provides an apparatus for use with a ventricular assist device (VAD). The apparatus comprises an inflow cannula having a first part for connecting with a ventricle of a heart and a second part for connecting with the VAD. A conduit made of a flexible material has oppositely disposed first and second ends and a main body portion intermediate the ends. The main body portion has an accordion-like configuration to allow for relative axial and radial movement of the ends. First connecting means connects the first end of the conduit to the first part of the inflow cannula. Second connecting means connects the second end of the conduit to the second part of the inflow cannula. The apparatus further comprises means for occluding blood flow through the inflow cannula.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a schematic illustration of a ventricular assist device (VAD) implanted in a human;

FIG. 2 is a side view of an inflow cannula shown in FIG. 1 and used in connection with the VAD of FIG. 1;

FIG. 3 is an exploded view of a portion of the inflow cannula shown in FIG. 2;

FIG. 7 is a perspective view of the components shown in FIG. 4 along with a clamp for occluding blood flow through the inflow cannula;

FIG. 8 is a sectional view taken along line 8—8 in FIG. 7;

FIG. 9 is a side view similar to FIG. 5 illustrating structure for holding the inflow cannula in an axially compressed position in accordance with a first embodiment of the present invention;

FIG. 11 is a side view similar to FIG. 10 and illustrating a plug for closing one end of the inflow cannula;

FIG. 13 is a side view similar to FIG. 11 illustrating structure for holding the inflow cannula in an axially compressed condition in accordance with a third embodiment of the present invention;

FIG. 14 is a sectional view of FIG. 13 showing the inflow cannula in an axially extended condition;

FIG. 15 is a view taken along line 15—15 in FIG. 13;

DESCRIPTION OF EMBODIMENTS

Figure 4:
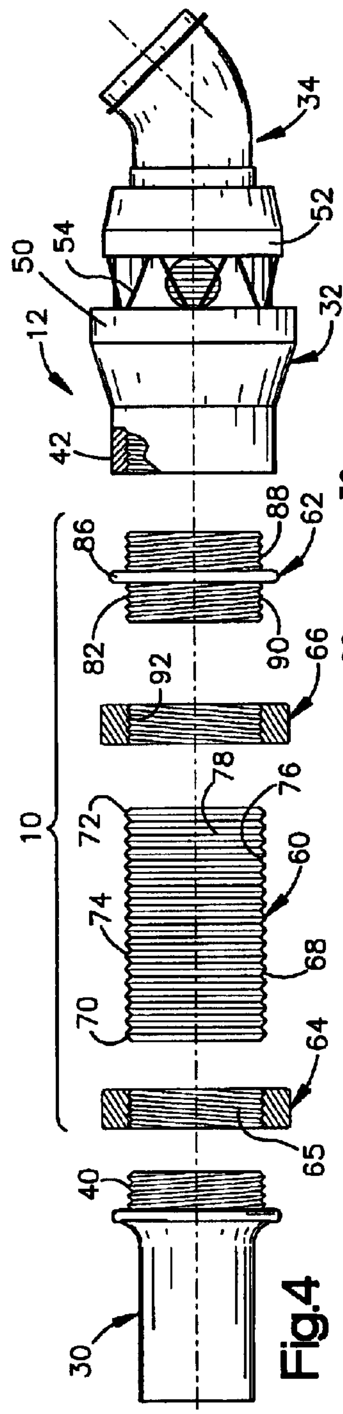
FIG. 4 is an exploded view showing the inflow cannula of FIG. 2 along with an apparatus for use with the inflow cannula in accordance with the present invention.

The present invention is directed to an apparatus 10 (FIG. 4) for use with an inflow cannula 12 of a ventricular assist device (VAD). FIG. 1 schematically illustrates a known VAD 14 implanted in a human patient. The illustrated VAD 14 is marketed under the trademark HeartMate® and is available from Thermo Cardiosystems, Inc. of Woburn, Mass. The VAD 14 includes the inflow cannula 12, a pump section 16, and an outflow cannula 18. The inflow cannula 12 attaches to an inlet side 20 of the pump section 16 and is connected with the ventricle 22 of the patient's heart 24. The outflow cannula 18 attaches to an outlet side 26 of the pump section 16 and is connected to the patient's aorta 28.

FIG. 2 is an enlarged view of the inflow cannula 12 that is typically used with the illustrated VAD 14. The inflow cannula 12 includes an inlet section 30, a valve section 32, and an outlet section 34 comprising an elbow. The inlet section 30 is a tubular conduit having oppositely disposed first and second ends 36 and 38 (FIG. 3). The first end 36 of the inlet section 30 has a straight configuration and is connected with the ventricle 22 by inserting the first end through an apical sewing ring (not shown) that has been sutured into an opening in the ventricle in a known manner. The second end 38 of the inlet section 30 has a flanged configuration and includes external threads 40 that connect with the valve section 32. An inner surface 37 extends between the ends 36 and 38 and defines a lumen 39 through the inlet section 30.

The valve section 32 is also a tubular conduit having oppositely disposed first and second ends 42 and 44. The first end 42 of the valve section 32 has internal threads 46 for mating with the external threads 40 on the second end 38 of the inlet section 30. The second end 44 of the valve section 32 has external threads 48 for mating with internal threads (not shown) on the outlet section 34 of the inflow cannula 12. A flexible lining (not shown) extends through the inside of the valve section. The flexible lining is made of a woven polyester fabric and is attached to the first and second ends 42 and 44 of the valve section 32 in a known manner. A valve (not shown), which is made of autogenous, bovine, porcine, artificial tissue, or a mechanical valve, is positioned inside the lining in the valve section 32.

The valve section 32 of the inflow cannula 12 includes first and second portions 50 and 52 (FIG. 2). A small amount of relative movement is permitted between the portions 50 and 52 of the valve section 32 to allow for positional (angular) adjustment. Such relative movement is restricted by sutures 54 that extend between the two portions 50 and 52 of the valve section 32.

In accordance with a first embodiment of the present invention, the apparatus 10 (FIG. 4) for use with the inflow cannula 12 comprises a flexible conduit 60, an adapter 62, and first and second nuts 64 and 66, respectively. The first nut 64 includes threads 65 designed to threadedly engage and mate with the external threads 40 on the second end 38 of the inlet section 30 of the inflow cannula 12.

The conduit 60 is a woven polyester fabric that is both resilient and flexible. The conduit 60 has a spiral pattern of continuous corrugations 68 that have an accordion-like configuration. It should be understood that the conduit 60 could alternatively be made of another suitable material. The corrugations 68 are sized so that they are physical similar to the size of the threads on the first and second nuts 64 and 66.

The conduit 60 has oppositely disposed first and second ends 70 and 72 and a main body portion 74 intermediate the ends. An inner surface 76 extends between the ends 70 and 72 of the conduit 60 and defines a lumen 78. The inner surface 76 of the conduit 60 may include a coating to resist thrombus formation and/or blood leakage.

The adapter 62 has inner and outer surfaces 80 and 82 (FIG. 6), respectively. The inner surface 80 defines a passage 84 through the adapter 62. The outer surface 82 includes a flange portion 86 and oppositely disposed first and second threaded portions 88 and 90, respectively. The first threaded portion 88 of the adapter 62 is designed to threadedly engage and mate with the internal threads 46 on the first end 42 of the valve section 32 of the inflow cannula 12. The second threaded portion 90 of the adapter 62 is designed to threadedly engage and mate with internal threads 92 on the second nut 66.

Figure 5:
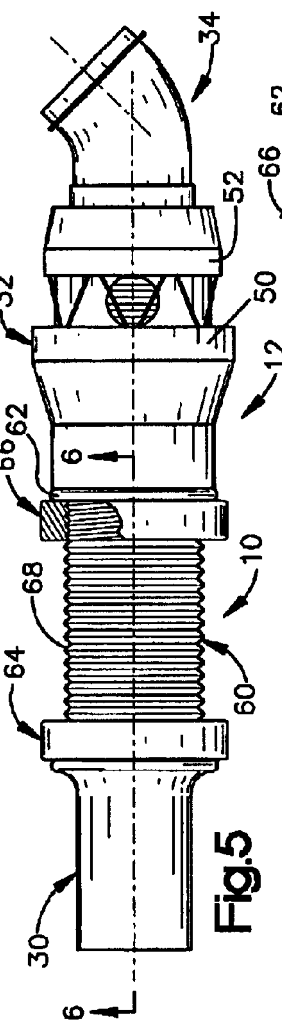
FIG. 5 is a side view showing the components of FIG. 4 in an assembled condition.

The apparatus 10 is assembled by unscrewing the inlet section 30 of the inflow cannula 12 from the valve section 32. The first threaded portion 88 of the adapter 62 is screwed into the first end 42 of the valve section 32 of the inflow cannula 12. The second end 72 of the conduit 60 is then placed over the second threaded portion 90 of the adapter 62. Next, the second nut 66 is disposed circumferentially about the second end 72 of the conduit 60 and is screwed onto the second threaded portion 90 of the adapter 62. Screwing the second nut 66 onto the second threaded portion 90 of the adapter 62 sandwiches the second end of the conduit between the threads 92 on the second nut and the second threaded portion, thereby securing the second end of the conduit to the adapter and to the valve section 32 of the inflow cannula 12, as shown in FIGS. 5 and 6.

The first end 70 of the conduit 60 is then placed over the threads 40 on the second end 38 of the inlet section 30 of the inflow cannula 12. Next, the first nut 64 is disposed circumferentially about the first end 70 of the conduit 60 and is screwed onto the threads 40 on the second end 38 of the inlet section 30. Screwing the first nut 64 onto the threads 40 on the second end 38 of the inlet section 30 sandwiches the first end 70 of the conduit 60 between the threads 65 on the first nut 64 and the threads 40 on the inlet section 30, thereby securing the first end of the conduit to the inlet section of the inflow cannula 12, as shown in FIGS. 5 and 6.

Figure 6:
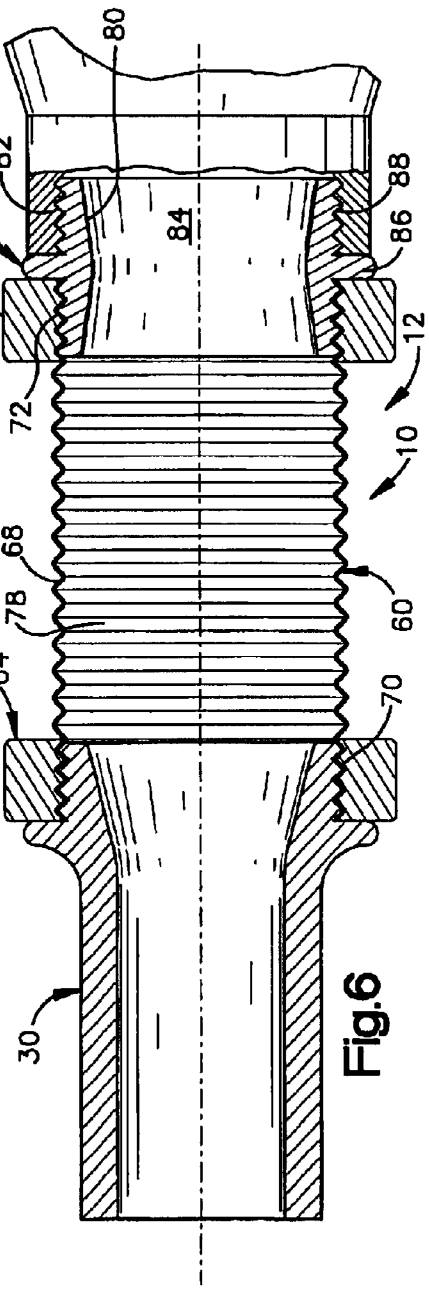
FIG. 6 is a sectional view taken along 6—6 in FIG. 5.

As shown in FIG. 6, the main body portion 68 of the conduit 60 has a radially open expanded condition. In this condition, blood from the left ventricle flows through the lumen 39 in the inlet section 30, through the lumen 78 in the conduit 60, and though the passage 84 in the adapter 62 into the valve section 32 without being blocked or occluded.

FIGS. 7 and 8 illustrate a radially collapsed closed condition for the main body portion of the conduit 60. In the illustrated closed condition, blood flow through the apparatus 10, and thus through the inflow cannula 12, is completely blocked or occluded. The closed condition is achieved by compressing the main body portion 68 of the conduit 60 with a surgical clamp 100. When the surgical clamp 100 is removed, the main body portion 68 of the conduit 60 returns to the open, expanded condition of FIG. 6.

The apparatus 10 thus provides the ability to temporarily occlude blood flow through the inflow cannula 12 to the VAD 14. This ability to occlude blood flow through the inflow cannula 12 can be useful in cases where the VAD 14 has allowed the heart to heal itself and the VAD is to be removed, as well as cases where the VAD remains implanted but requires service or replacement of certain parts.

FIG. 9 illustrates a first embodiment of another feature of the invention. As may be seen in FIG. 9, the apparatus 10 further includes a sleeve 110 disposed circumferentially about the first and second nuts 64 and 66. The sleeve 110 has a clamshell-style configuration with upper and lower sections 112 and 114 connected by a hinge (not shown) that allows the sleeve to open up and slide over the nuts 64 and 66. The sleeve 110 may also include a clasp feature (not shown) for securing the sections 112 of the sleeve together about the nuts 64 and 66.

When installed, the sleeve 110 holds the nuts 64 and 66 in the positions shown in FIG. 9 and maintains the conduit 60 in an axially compressed condition. By holding the nuts 64 and 66 in the positions of FIG. 9, the sleeve prevents relative axial and radial movement of the ends 70 and 72 of the conduit 60 away from each other. Depending on the particulars of the implantation of the inflow cannula 12 and the VAD 14, it may be desirable to install the sleeve 110 prior to implantation, or during implantation, to prevent flexing of the conduit 60. Further, the sleeve 110 can be used to rigidly connect the inlet section 30 to the valve section 32. Such a rigid connection can be useful if the inlet section 30 is to be temporarily capped off, as is described further below, in order to repair or replace the VAD 14. The rigid connection between the inlet and valve sections 30 and 32 may also be desirable when the inflow cannula 12 is to be permanently capped off, but remain attached to the ventricle 22, because the VAD 14 is being removed.

Figure 10:
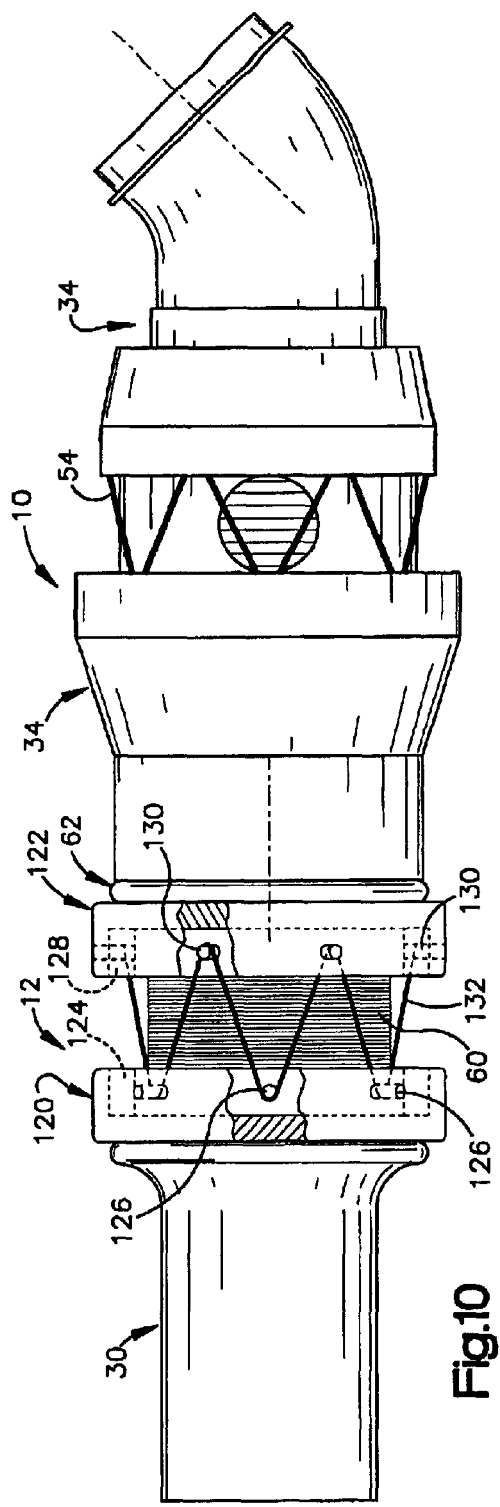
FIG. 10 is a side view similar to FIG. 9 illustrating structure for holding the inflow cannula in an axially compressed condition in accordance with a second embodiment of the present invention.

FIG. 10 illustrates an alternative means for holding the conduit 60 in the axially compressed condition and for preventing relative movement of the ends 70 and 72 of the conduit in accordance with a second embodiment of the invention. In the embodiment of FIG. 10, the apparatus 10 includes first and second nuts 120 and 122 that are slightly different than the first and second nuts 64 and 66 described above. The first nut 120 has an annular chamber 124 and a plurality of pins 126 that extend radially through the chamber. Similarly, the second nut 122 has an annular chamber 128 and a plurality of pins 130 that extend radially through the chamber. A suture 132 is wrapped around the pins 126 and 130 in the first and second nuts 120 and 122, respectively, in an alternating fashion as shown in FIG. 10 to secure the first and second nuts to each other. When connected by the suture 132, the nuts 120 and 122 maintain the conduit 60 in an axially compressed condition and prevent relative axial and radial movement of the ends 70 and 72 of the conduit away from each other.

Figure 12:
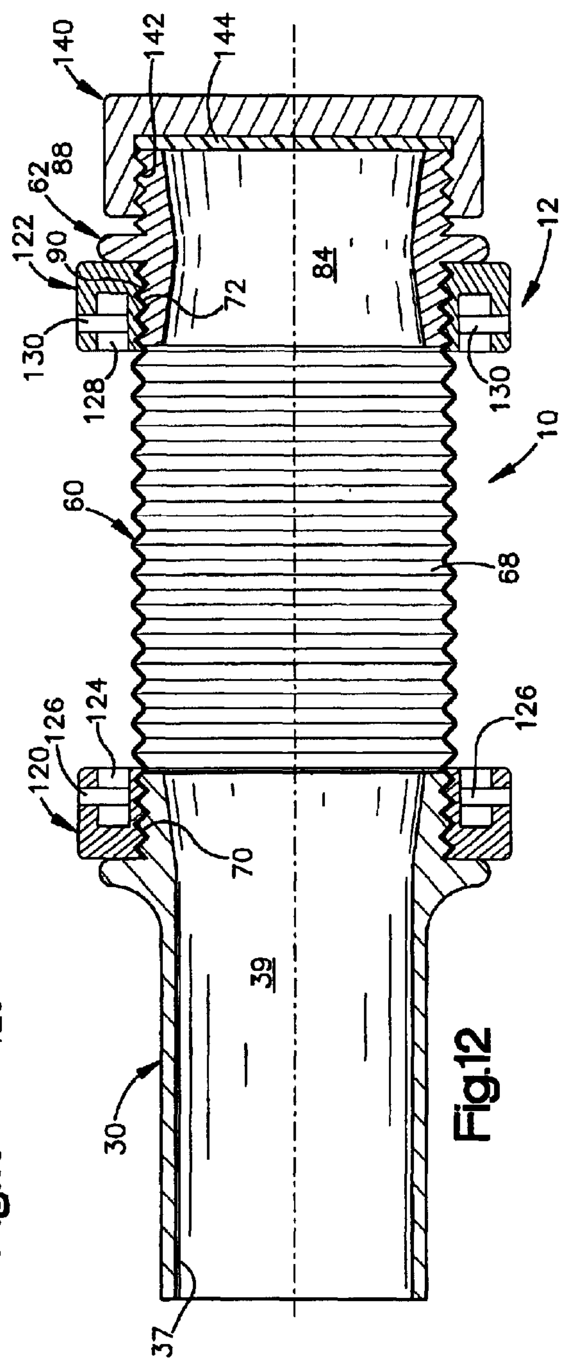
FIG. 12 is a sectional view of FIG. 11 showing the inflow cannula in an axially extended condition.

FIGS. 11 and 12 illustrate the apparatus 10 with an alternate means for occluding blood flow through the inflow cannula 12. As shown in FIGS. 11 and 12, a plug 140 having internal threads 142 is screwed onto the first threaded portion 88 of the adapter 62. A seal 144 may be located inside the plug 140 to prevent any leakage of blood. The plug 140 is used to permanently cap off, and thus block, the flow of blood through the conduit 60 and the inflow cannula 12.

The plug 140 may be used in a situation where the heart 24 has healed itself to the point where the VAD 14 can be removed, but the physician prefers to leave the inflow cannula 12 attached to the left ventricle 22. In such a case, it is likely that the clamp 100 (FIG. 7) would be used to temporarily block the flow of blood through the inflow cannula 12 while the valve section 32 of the inflow cannula 12 is unscrewed from the adapter 62. The plug 140 would then be screwed onto the adapter 62, and the clamp 100 would be released. As shown in FIG. 11, it may be desirable to secure the first and second nuts 120 and 122 to each other, using the suture 132 or other means, when the plug 140 is installed to restrict movement of the adapter 62 and the plug.

FIGS. 13–15 illustrates yet another alternative means for holding the conduit 60 in the axially compressed condition and for preventing relative movement of the ends 70 and 72 of the conduit in accordance with a third embodiment of the invention. In the embodiment of FIGS. 13–15, the apparatus 10 includes first and second nuts 150 and 152 that differ from the nuts previously described, and further includes a collar 154 that connects the first and second nuts 150 and 152 as described below.

The first nut 150 includes an annular chamber 156 and a plurality of J-shaped slots 158 (FIG. 15) that extend between an outer surface 160 and the chamber. The second nut 152 includes a radially outwardly extending flange 162. The collar 154 is cylindrical in shape and has oppositely disposed first and second ends 164 and 166. Adjacent the first end 164, the collar 154 includes a plurality of inwardly projecting pin members 168 that are sized and located so as to engage the J-shaped slots 158 on the first nut 150. The second end 166 of the collar 154 includes a radially inwardly extending flange 170 that engages the flange 162 on the second nut 152.

As best seen in FIGS. 13 and 15, to interconnect the first and second nuts 150 and 152, the pins 168 on the collar 154 are inserted into the slots 158 in the first nut and the collar is rotated so that each of the pins comes to rest in an end portion 172 of each of the slots. With the nuts 150 and 152 connected by the collar 154, the conduit 60 is maintained in an axially compressed condition and relative axial and radial movement of the ends 70 and 72 of the conduit away from each other is prevented.

Figure 16:
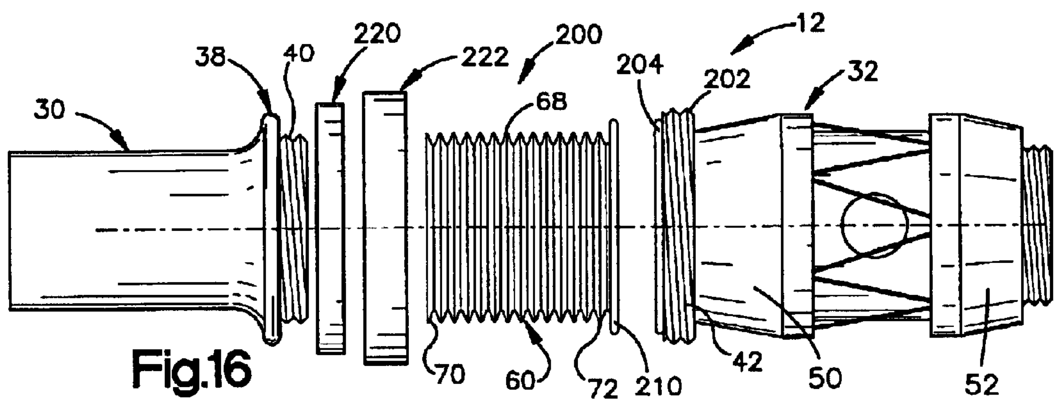
FIG. 16 is an exploded view showing the inflow cannula of FIG. 2 along with an apparatus for use with the inflow cannula in accordance with an alternate construction of the present invention.
Figure 17:
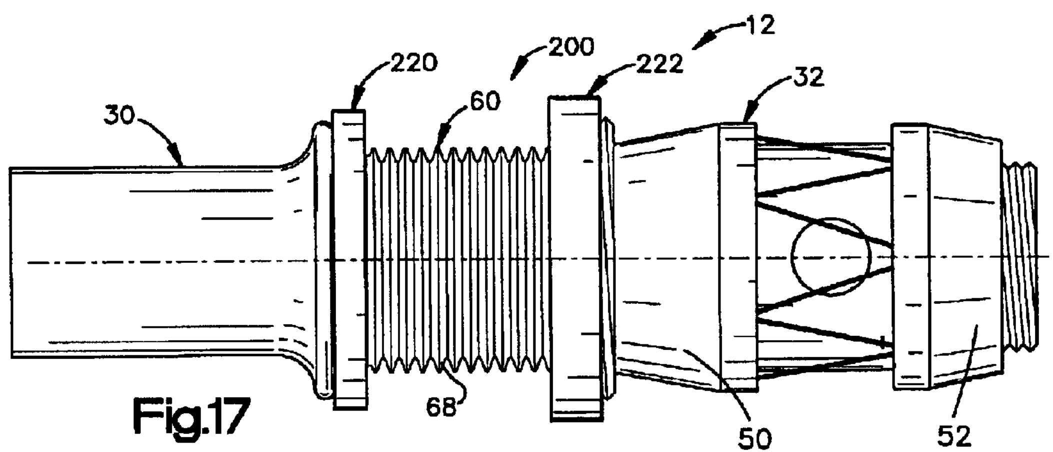
FIG. 17 is a side view showing the components of FIG. 16 in an assembled condition.
Figure 18:
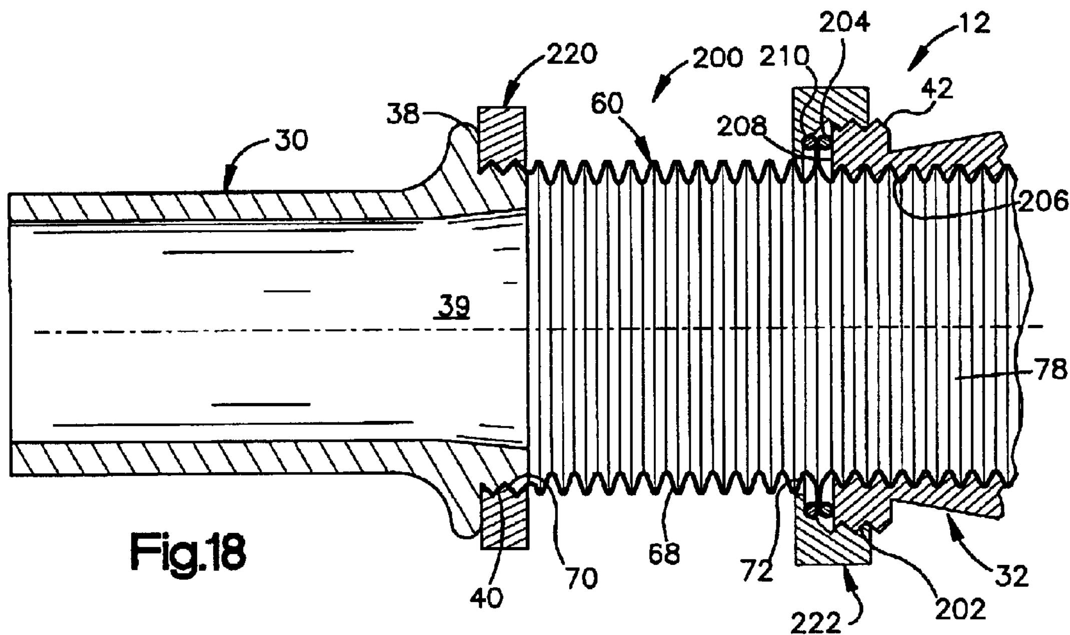
FIG. 18 is a sectional view of a portion of FIG. 17.

FIGS. 16–18 illustrate an apparatus 200 for use with the inflow cannula 12 in accordance with an alternate construction of the present invention. As may be seen in FIG. 16, external threads 202 have been added to the first end 42 of the valve section 32. A first sealing ring 204, which is sutured to a flexible conduit 206 (FIG. 18) running through the valve section 32, abuts a radially extending outer surface 208 of the valve section. A second sealing ring 210 is sutured to the second end 72 of the flexible conduit 60.

The apparatus includes first and second nuts 220 and 222. The first nut 220 is designed to threadedly engage and mate with the external threads 40 on the second end 38 of the inlet section 30 of the inflow cannula 12. The second nut 222 is designed to threadedly engage and mate with the external threads 202 on the first end 42 of the valve section 32 of the inflow cannula 12.

The apparatus 200 is assembled by unscrewing the inlet section 30 of the inflow cannula 12 from the valve section 32. The second nut 222 is disposed circumferentially about the second end 72 of the conduit 60 and is screwed onto the threads 202 on the valve section 32. In screwing the second nut 222 to the valve section 32, the second sealing ring 210 at the second end 72 of the conduit 60 is captured by the second nut and is pressed against the first sealing ring 204, thereby securing the second end 72 of the conduit to the valve section of the inflow cannula 12, as may be seen in FIGS. 17 and 18.

The first end 70 of the conduit 60 is then placed over the threads 40 on the second end 38 of the inlet section 30 of the inflow cannula 12. Next, the first nut 220 is disposed circumferentially about the first end 70 of the conduit 60 and is screwed onto the threads 40 on the second end 38 of the inlet section 12. Screwing the first nut 220 onto the threads 40 on the inlet section 30 sandwiches the first end 70 of the conduit 60 between the threads on the first nut and the threads on the inlet section, thereby securing the first end of the conduit to the inlet section of the inflow cannula 12.

As with the previously described embodiments, the main body portion 60 of the conduit 60 has a radially open expanded condition. In this condition, blood from the left ventricle 22 flows through the lumen 39 in the inlet section 30, through the lumen 78 in the conduit 60, and into the valve section 32 without being blocked or occluded. The main body portion 68 of the conduit 60 also has a radially collapsed closed condition in which blood flow through the apparatus 200, and thus through the inflow cannula 12, is completely blocked or occluded. The closed condition is achieved by compressing the main body portion 68 of the conduit 60 with the surgical clamp 100 shown in FIG. 7. When the surgical clamp 100 is removed, the main body portion 68 of the conduit 60 returns to the open, expanded condition.

The apparatus 200 thus provides the ability to temporarily occlude blood flow through the inflow cannula 12 to the VAD 14. This ability to occlude blood flow through the inflow cannula 12 can be useful in cases where the VAD 14 has allowed the heart 24 to heal itself and the VAD is to be removed, as well as cases where the VAD remains implanted but requires service or replacement of certain parts.

Figure 19:
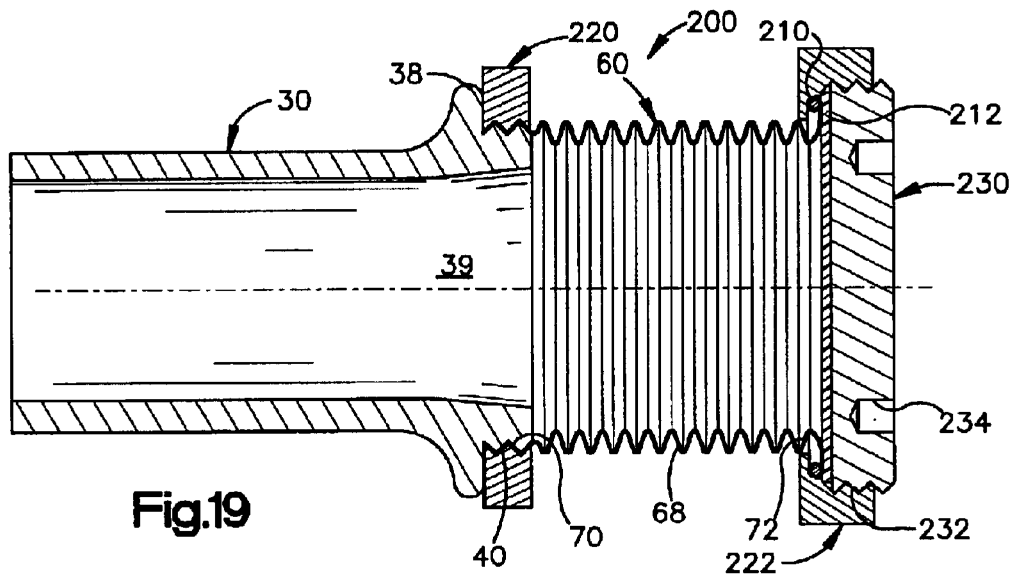
FIG. 19 is a sectional view similar to FIG. 18 illustrating a plug for closing one end of the inflow cannula.

FIG. 19 illustrates the apparatus 200 with an alternate means for occluding blood flow through the inflow cannula 12. As shown in FIG. 19, a plug 230 having external threads 232 is screwed into the second nut 222. Seals 210 and 212 prevent any leakage of blood. The plug 230 also includes a plurality of axially extending openings 234 for receiving a spanner wrench (not shown). The plug 230 is used to permanently cap off, and thus block, the flow of blood through the conduit 60 and the inflow cannula 12.

The plug 230 may be used in a situation where the heart 24 has healed itself to the point where the VAD 14 can be removed, but the physician prefers to leave the inflow cannula 12 attached to the ventricle 22. In such a case, it is likely that the clamp 100 (FIG. 7) would be used to temporarily block the flow of blood through the inflow cannula 12 while the valve section 32 of the inflow cannula 12 is unscrewed from the nut 222. The plug 230 would then be screwed onto the nut 222, and the clamp 100 would be released.

As discussed previously, it may be desirable to secure the first and second nuts 220 and 222 to each other, using a suture or other means, when the plug 230 is installed to restrict movement of the conduit 60 and the plug.

For example, it should be understood that the first and second nuts 220 and 222 could be modified to include the pins 126 and 128, respectively, and the suture 132, shown in FIGS. 10–12, for holding the nuts together. Further, the nuts 220 and 222 could also be modified to utilize the collar 154 illustrated in FIGS. 13–15 to hold the nuts together.

Figure 20:
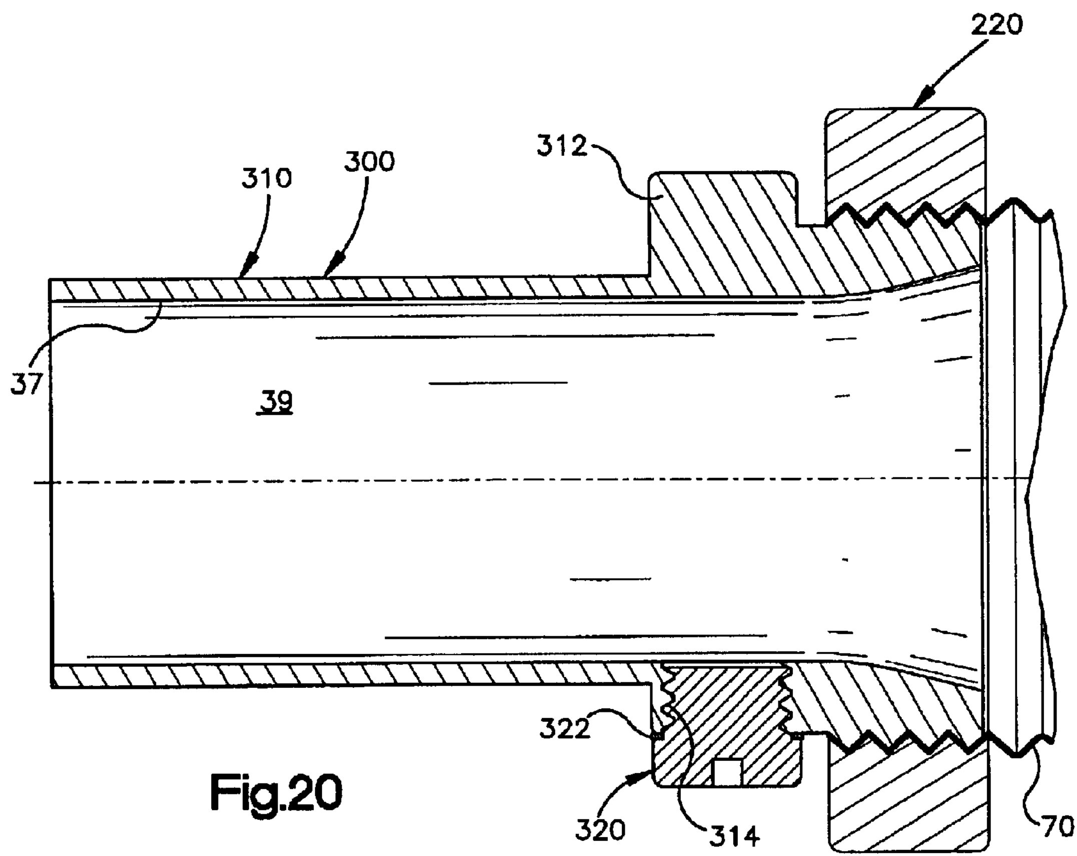
FIG. 20 is a sectional view similar to a portion of FIG. 2 illustrating a modified version of the inflow cannula that is occludable using a balloon.
Figure 21A:
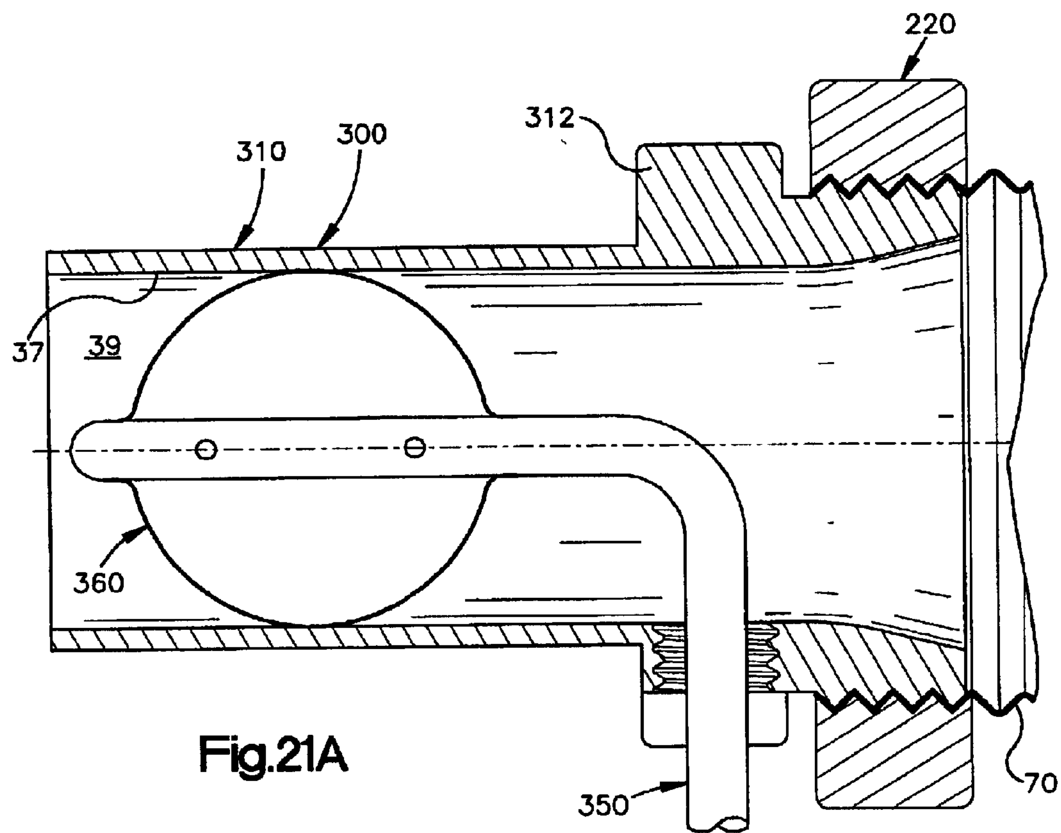
FIG. 21A is a sectional view of a portion of FIG. 20 showing an occlusion balloon in a first position.
Figure 21B:
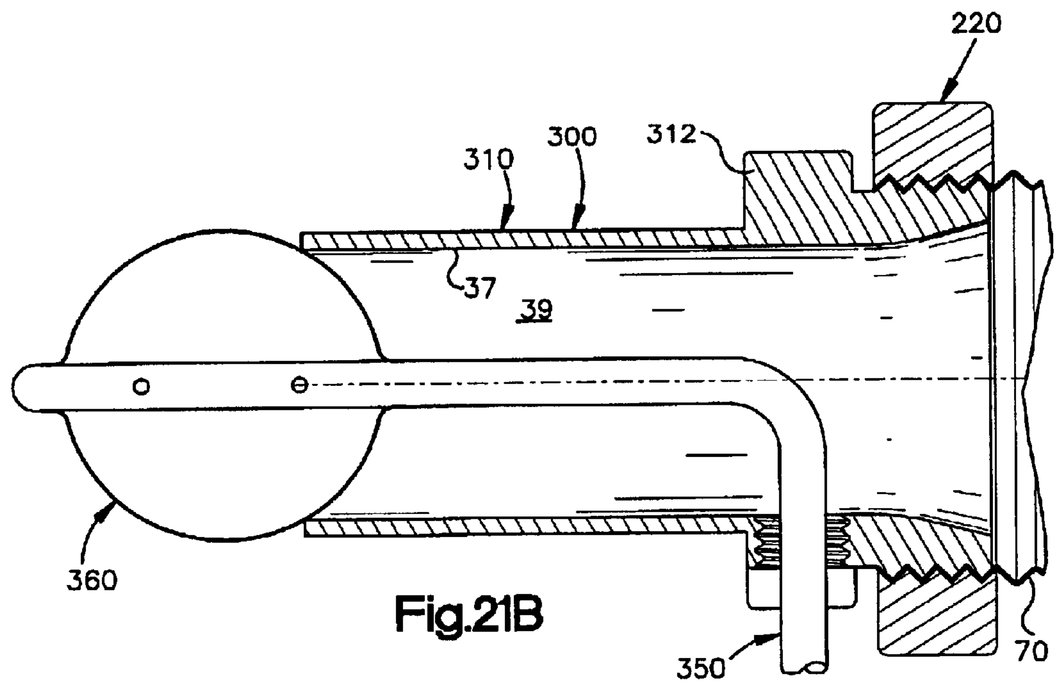
FIG. 21B is a sectional view of a portion of FIG. 20 showing an occlusion balloon in a second position.
Figure 21C:
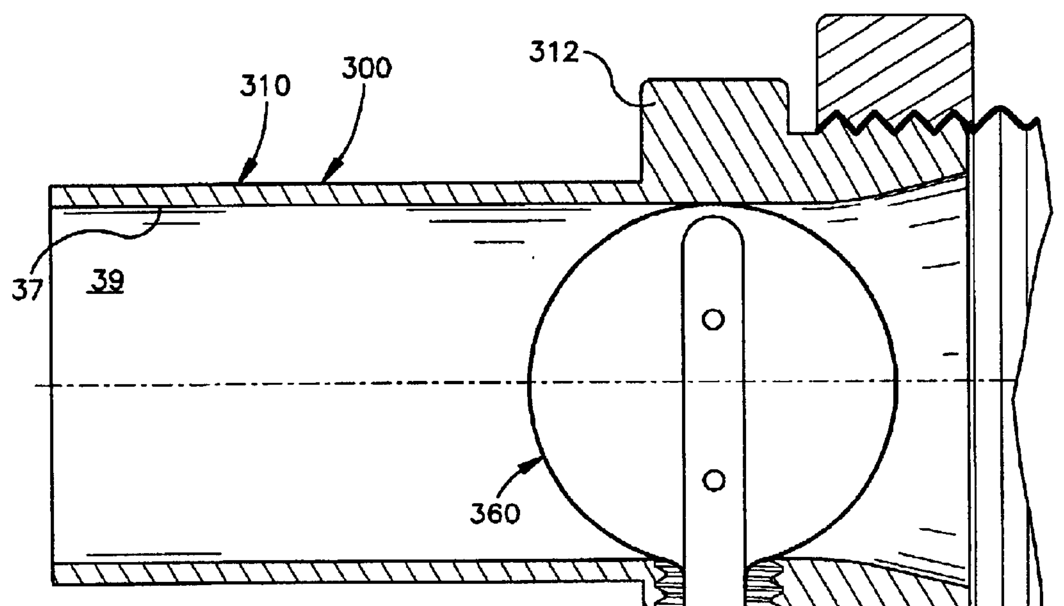
FIG. 21C is a sectional view of a portion of FIG. 20 showing an occlusion balloon in a third position.

FIGS. 20–21C illustrate an apparatus 300 that includes an inlet section 310 that has been modified slightly from the inlet section 30 described previously so that the inlet section is occludable using a balloon 360. In the embodiment of FIGS. 20–21C, reference numbers that are the same as those used in the previous embodiments identify structure that is the same as described in the previous embodiments.

The second end 38 of the inlet section 310 includes a thick flange 312 that has a radially extending threaded opening 314. The threaded opening 314 receives a screw 320. The innermost surface of the screw 320 that faces inside the inlet section 310 is sintered just like the inner surface of the inlet section. A gasket 322 may be placed under the head of the screw 320 to improve sealing.

When occlusion of the inlet section 310 is desired, the screw 320 is removed and a catheter 350 carrying the balloon 360 is inserted into the lumen 39 through the opening 314. The balloon 360 is then inflated until blood flow through the inlet section 310 is blocked. As may be seen in FIGS. 21A–21C, the balloon 360 may positioned in a number of locations based on how far the catheter 350 is inserted into the lumen 39.

Figure 22:
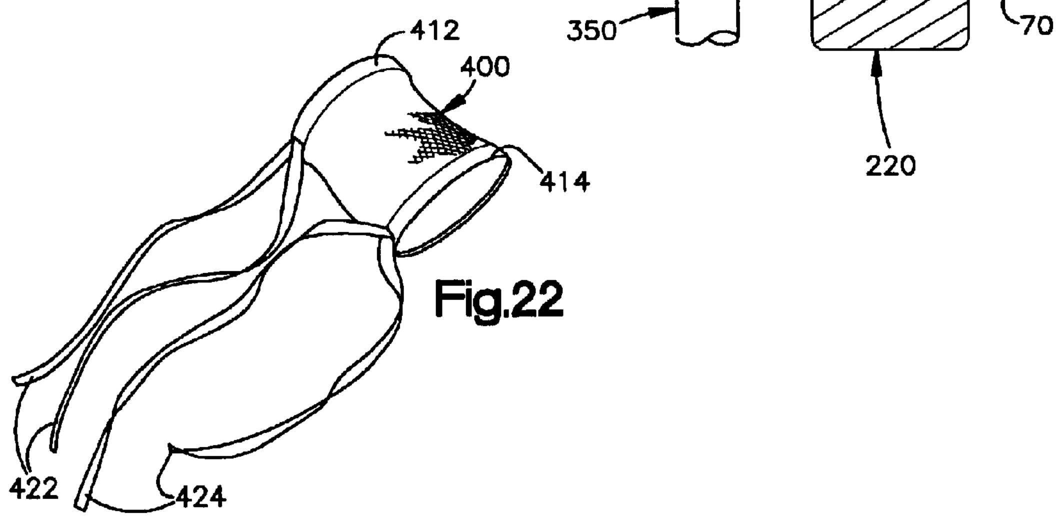
FIG. 22 is a perspective view illustrating a fabric sheath for holding the inflow cannula in an axially compressed condition in accordance with a fourth embodiment of the present invention.
Figure 23:
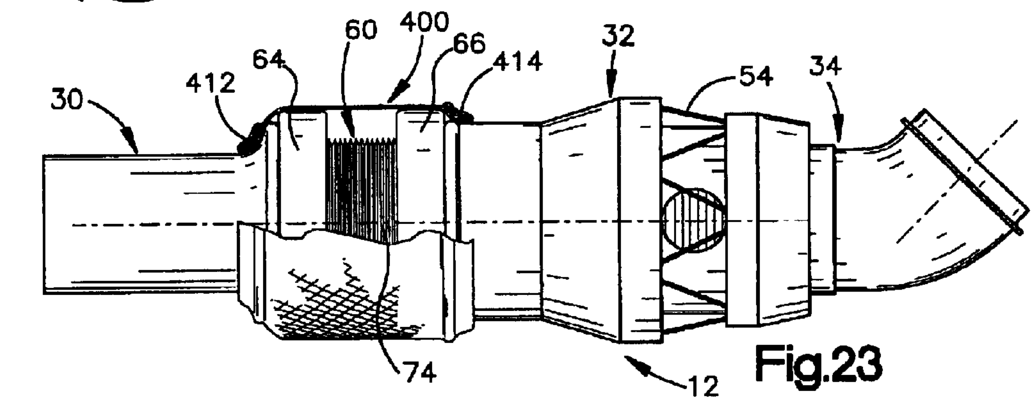
FIG. 23 is a side view similar to FIG. 6 showing the sheath of FIG. 22 holding the inflow cannula in an axially compressed condition.

FIGS. 22 and 23 illustrate a fourth embodiment of a feature for holding the inflow cannula 12 in an axially compressed condition. According to the fourth embodiment, a sheath 400 made of polyester fabric is disposed circumferentially about the first and second nuts 64 and 66. The sheath 400 has a tubular configuration with oppositely disposed first and second end sections 412 and 414. The first end section 412 has a drawstring 422 for radially tightening the first end section. The second end section 414 has a drawstring 424 for radially tightening the second end section.

The sheath 400 is installed by sliding it axially over the nuts 64 and 66 and the main body portion 74 of the conduit 60. The drawstrings 422 and 424 at the end sections 412 and 414, respectively, of the sheath 400 are then pulled tight around the nuts 64 and 66, respectively, and tied. The loose ends of the drawstrings 422 and 424 can then be cutoff, if desired.

Once installed, the sheath 400 holds the nuts 64 and 66 in the positions shown in FIG. 23 and maintains the conduit 60 in an axially compressed condition. By holding the nuts 64 and 66 in the positions of FIG. 23, the sheath 400 prevents relative axial and radial movement of the ends 70 and 72 of the conduit 60 away from each other.

Figure 24:
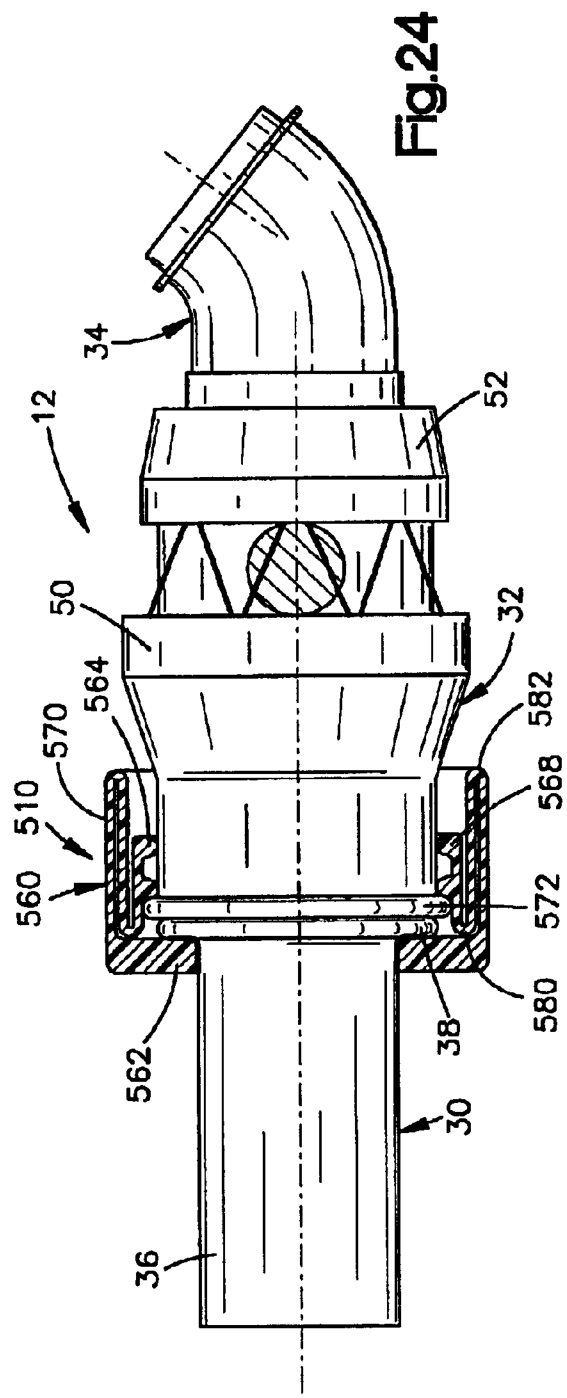
FIG. 24 is a side view illustrating an apparatus for use with the inflow cannula in accordance with a fifth embodiment of the present invention.

In accordance with a fifth embodiment of the present invention, an apparatus 510 (FIG. 24) for use with the inflow cannula 12 comprises a flexible conduit 560, having oppositely disposed first and second ends 562 and 564, respectively. The first end 562 is bonded, using a silicone adhesive or other suitable alternative, to the outer surface of the inlet section 30 of the inflow cannula 12 and the surface of the flange. The second end 564 comprises a rotating seal 568 that sealingly engages the outer surface of the valve section 32 of the inflow cannula 12 and allows relative rotation between the valve section and the seal. The seal 568 is positioned behind a flange 572 at the first end 42 of the valve section 32. It is contemplated that a support ring or other suitable means could be positioned around the outside of the rotating seal 568.

The conduit 560 is made of a silicone rubber material that is both resilient and flexible. It should be understood that the conduit 560 could alternatively be made of another suitable material. The conduit 560 has a main body portion 570 intermediate the ends 562 and 564. An inner surface 576 (FIG. 25) extends between the ends 562 and 564 of the conduit 560 and defines a lumen 578. The inner surface 576 of the conduit 560 may include a coating to resist thrombus formation and/or blood leakage. The main body portion 570 of the conduit 560 has first and second axial folds 580 and 582, but it should be understood that the main body portion could have more or less than two folds.

Figure 25:
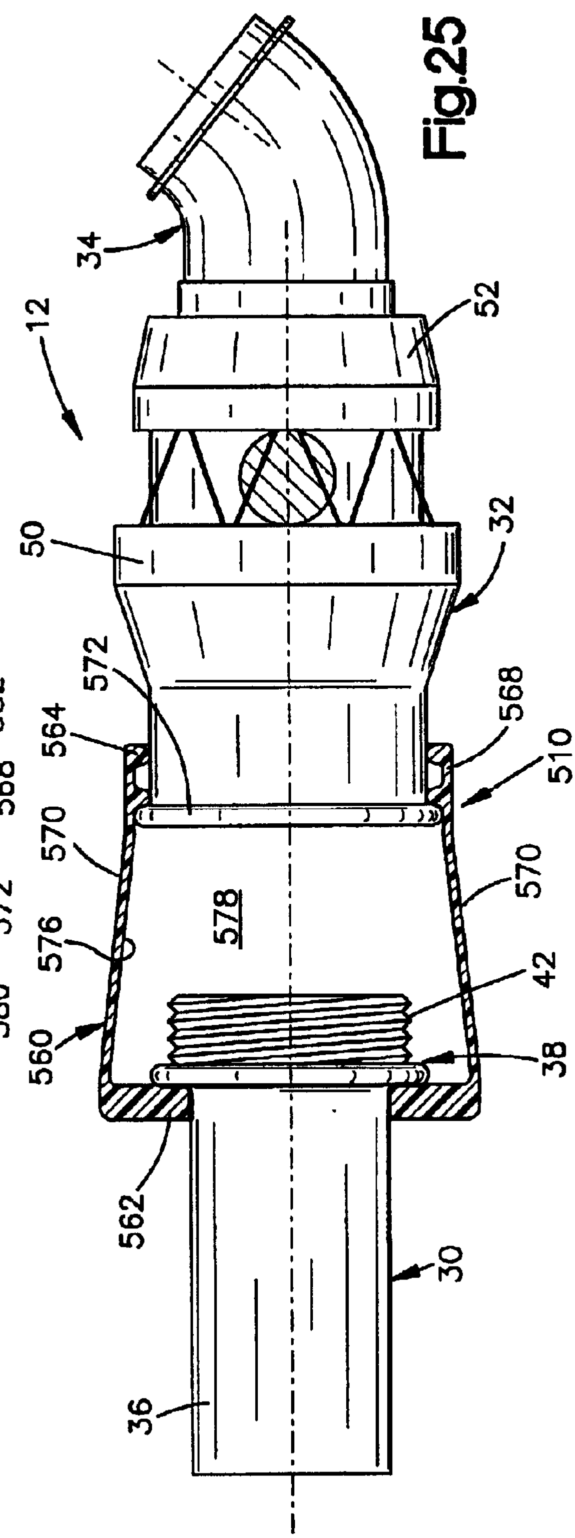
FIG. 25 is a side view similar to FIG. 24 showing the apparatus in an axially extended condition.

As shown in FIG. 25, the main body portion 570 of the conduit 560 has a radially open expanded condition. In this condition, blood from the left ventricle flows through the lumen 39 in the inlet section 30, through the lumen 578 in the conduit 560, and into the valve section 32 without being blocked or occluded.

Figure 26:
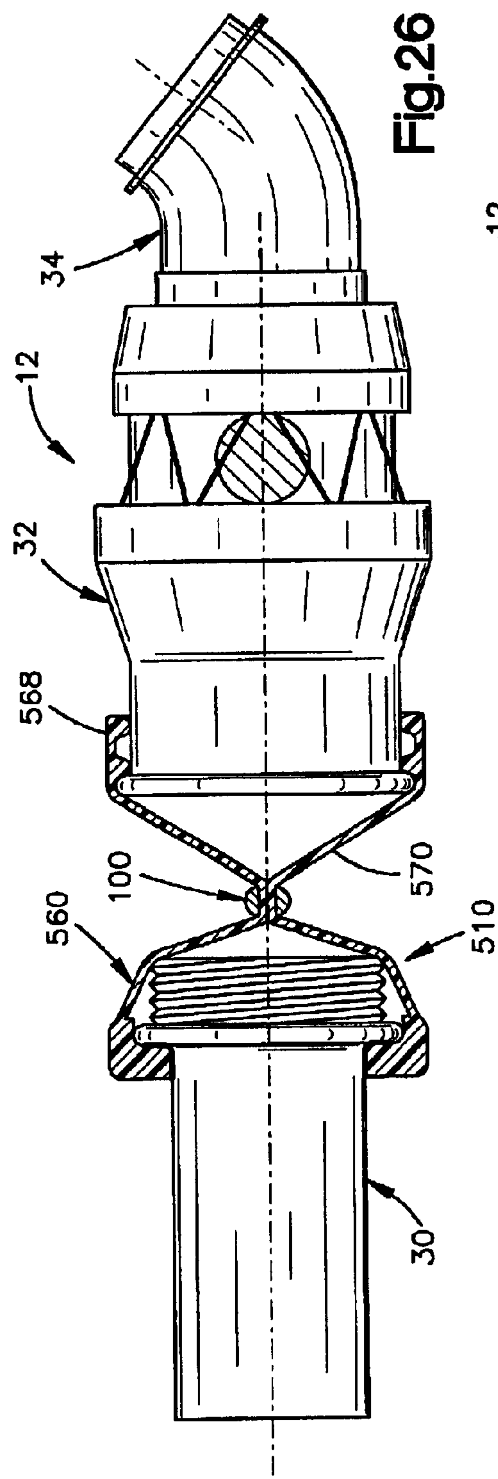
FIG. 26 is a side view similar to FIG. 24 showing the apparatus in a radially collapsed condition.
Figure 27:
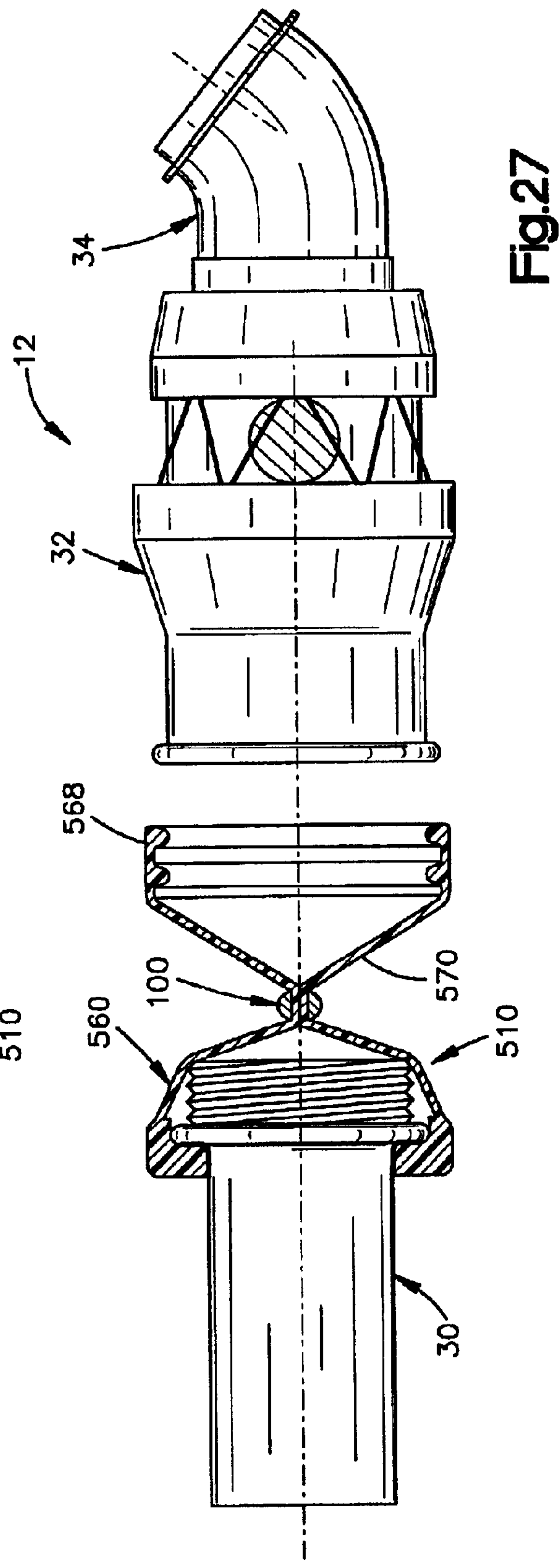
FIG. 27 is a side view similar to FIG. 26 showing the apparatus detached from a part of the inflow cannula.

FIGS. 26 and 27 illustrate a radially collapsed closed condition for the main body portion of the conduit 560. In the illustrated closed condition, blood flow through the apparatus 510, and thus through the inflow cannula 12, is completely blocked or occluded. The closed condition is achieved by compressing the main body portion 570 of the conduit 560 with the surgical clamp 100 shown in detail in FIG. 7. When the surgical clamp 100 is removed, the main body portion 570 of the conduit 560 returns to the open, expanded condition of FIG. 25.

The apparatus 510 thus provides the ability to temporarily occlude blood flow through the inflow cannula 12 to the VAD 14. This ability to occlude blood flow through the inflow cannula 12 can be useful in cases where the VAD 14 has allowed the heart to heal itself and the VAD is to be removed, as well as cases where the VAD remains implanted but requires service or replacement of certain parts.

Figure 28:
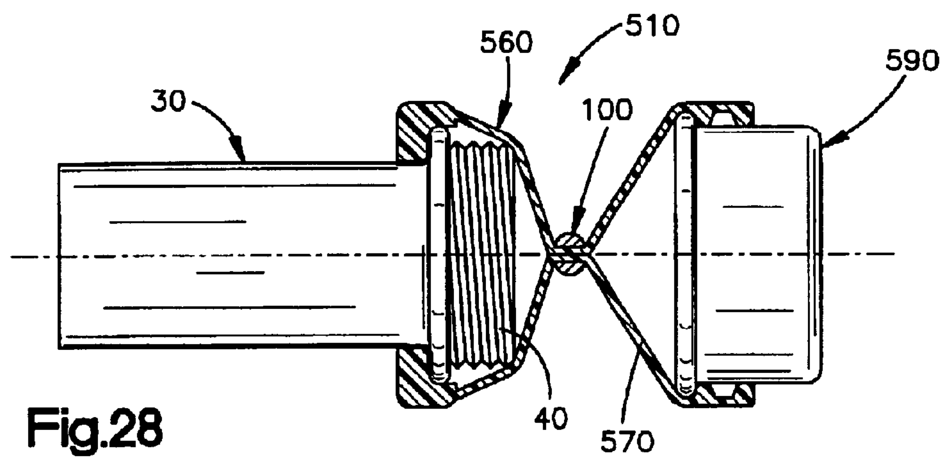
FIG. 28 is a side view similar to FIG. 27 and illustrating a plug for closing one end of the inflow cannula.
Figure 29:
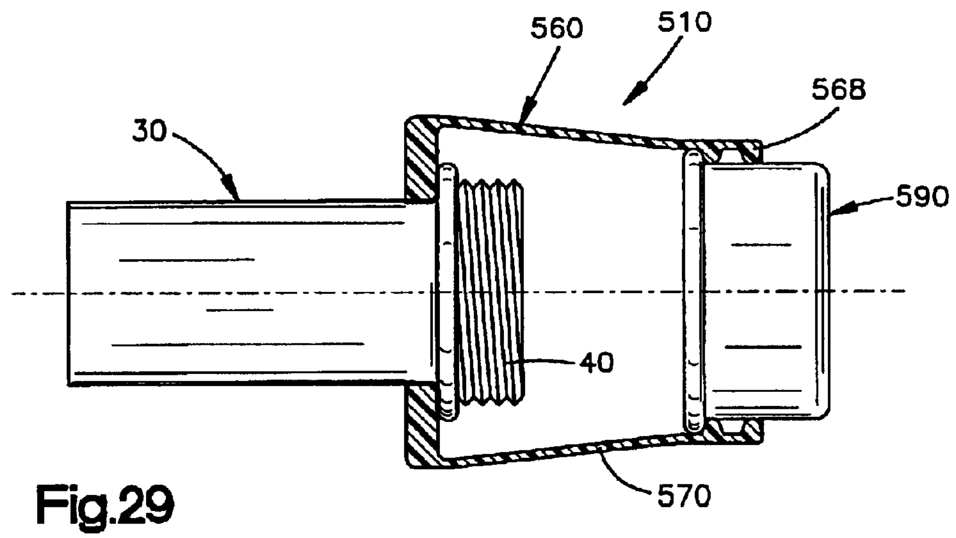
FIG. 29 is a side view similar to FIG. 28 showing the apparatus in the axially extended condition along with the plug.
Figure 30:
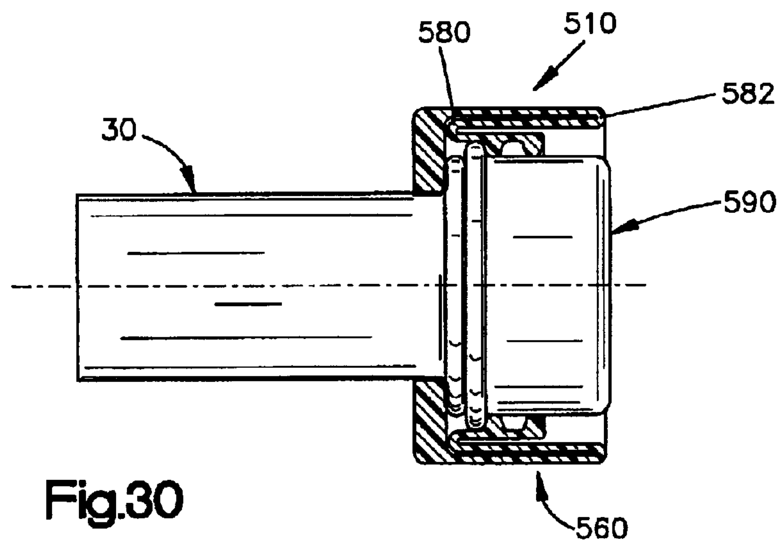
FIG. 30 is a side view similar to FIG. 29 showing the apparatus in the axially collapsed condition along with the plug.

FIGS. 28 and 30 illustrate the apparatus 510 with an alternate means for occluding blood flow through the inflow cannula 12. As shown in FIGS. 28–30, a plug 590 is attached to the seal 568 at the second end 564 of the conduit 560. The plug 590 can have internal threads (not shown) for mating with the threads 40 on the inlet section 30. The plug 590 is used to permanently cap off, and thus block, the flow of blood through the conduit 560 and the inflow cannula 12.

The plug 590 may be used in a situation where the heart 24 has healed itself to the point where the VAD 14 can be removed, but the physician prefers to leave the inflow cannula 12 attached to the left ventricle 22. In such a case, it is likely that the clamp 100 would be used to temporarily block the flow of blood through the inflow cannula 12 while the valve section 32 of the inflow cannula 12 is unscrewed from the inlet section 30. The valve section 32 can then be detached from the seal 568 of the conduit 560. The plug 590 would then be inserted into the seal 568 as shown in FIG. 28, and the clamp 100 would be released, as shown in FIG. 29. The plug 590 can then be screwed onto the threads 40 on the inlet section 30, as shown in FIG. 30.

From the above description of the invention, those skilled in the art will perceive improvements, changes and modifications. For example, it should be understood that the apparatuses described above could be modified to adapt to the specific geometry of the inflow cannulas used by other known VAD's such as the Novacor® device and HeartSaverVAD™ made by the World Heart Corporation of Ottawa, Canada, the Coraide™ and LionHeart™ devices produced by Arrow International of Reading, Pa., the MicroMed DeBakey VAD® made by MicroMed Technology Inc. of Houston, Tex., the HeartQuest™ device made by Medquest Products Inc. of Salt Lake City, Utah, and, of course, the other HeartMate® devices made by Thermo Cardiosystems, Inc. of Woburn, Mass. Such improvements, changes and modifications within the skill of the art are intended to be covered by the appended claims.

Having described the invention, we claim:

1. An apparatus for use with an inflow cannula of a ventricular assist device (VAD), the inflow cannula having a first part for connecting with a ventricle of a heart and a second part for connecting with the VAD, said apparatus comprising:

a conduit made of a flexible material, said conduit having oppositely disposed first and second ends and a main body portion intermediate said ends, said main body portion of said conduit being movable between a radially collapsed closed condition in which blood flow through said conduit is blocked and a radially expanded open condition in which blood flow through said conduit is not blocked;

first connecting means for connecting said first end of said conduit to the first part of the inflow cannula; and second connecting means for connecting said second end of said conduit to the second part of the inflow cannula;

said first connecting means comprises a first nut for threadedly engaging threads on the first part on the inflow cannula;

said second connecting means comprises a second nut and a threaded adapter, said adapter having a first threaded portion for engaging threads on the second part of the inflow cannula and a second threaded portion for threadedly engaging said second nut.

2. The apparatus of claim 1 wherein said main body portion of said conduit has an accordion-like configuration to allow for relative axial and radial movement of said ends.

3. The apparatus of claim 1 wherein said first end of said conduit is sandwiched between threads on said first nut and the threads on the first part of the inflow cannula.

4. The apparatus of claim 1 wherein said second end of said conduit is sandwiched between threads on said second nut and said second threaded portion on said adapter.

5. The apparatus of claim 1 further comprising means for occluding blood flow through said conduit.

6. The apparatus of claim 5 wherein said means for occluding blood flow comprises a surgical clamp.

7. The apparatus of claim 5 wherein said means for occluding blood flow comprises a threaded plug connected to said second connecting means.

8. The apparatus of claim 1 further comprising means for preventing relative axial and radial movement of said ends of said conduit away from each other.

9. The apparatus of claim 8 wherein said means for preventing movement of said ends comprises at least one suture that extends between said first and second connecting means and secure said first and second connecting means to each other.

10. The apparatus of claim 8 wherein said means for preventing movement of said ends comprises a collar that connects said first and second connecting means to each other, the collar having pin members that are sized and located to engage slots on the first nut.

11. The apparatus of claim 1 wherein said first connecting means comprises an adhesive for bonding said first end of said conduit to the first part on the inflow cannula.

12. The apparatus of claim 11 wherein said second connecting means comprises a rotating seal disposed at said second end of said conduit, said rotating seal for sealingly engaging the second part of the inflow cannula and allowing rotation of the second part relative to said rotating seal.

13. An apparatus for use with an inflow cannula of a ventricular assist device (VAD), the inflow cannula having a first part for connecting with a ventricle of a heart and a second cart for connecting with the VAD, said apparatus comprising:

a conduit made of a flexible material, said conduit having oppositely disposed first and second ends and a main body portion intermediate said ends, said main body portion of said conduit being movable between a radially collapsed closed condition in which blood flow through said conduit is blocked and a radially expanded open condition in which blood flow through said conduit is not blocked;

first connecting means for connecting said first end of said conduit to the first cart of the inflow cannula; and second connecting means for connecting said second end of said conduit to the second part of the inflow cannula;

means for preventing relative axial and radial movement of said ends of said conduit away from each other comprising a hinged clamshell-style sleeve that encloses said first and second connecting means and holds said main body portion of said conduit in an axially compressed condition.

14. An apparatus for use with an inflow cannula of a ventricular assist device (VAD), the inflow cannula having a first part for connecting with a ventricle of a heart and a second part for connecting with the VAD, said apparatus comprising:

a conduit made of a flexible material, said conduit having oppositely disposed first and second ends and a main body portion intermediate said ends, said main body portion of said conduit being movable between a radially collapsed closed condition in which blood flow through said conduit is blocked and a radially expanded open condition in which blood flow through said conduit is not blocked;

first connecting means for connecting said first end of said conduit to the first cart of the inflow cannula; and second connecting means for connecting said second end of said conduit to the second part of the inflow cannula;

means for preventing relative axial and radial movement of said ends of said conduit away from each other comprising a fabric sheath that encloses said first and second connecting means and holds said main body portion of said conduit in an axially compressed condition.

15. An apparatus for use with an inflow cannula of a ventricular assist device (VAD), the inflow cannula having a first part for connecting with a ventricle of a heart and a second part for connecting with the VAD, said apparatus comprising:

a conduit having oppositely disposed first and second ends and a main body portion intermediate said ends, said main body portion having a resiliently flexible section that is compressible to a closed condition in which blood flow through said conduit is blocked;

first connecting means for connecting said first end of said conduit to the first part of the inflow cannula; and second connecting means for connecting said second end of said conduit to the second part of the inflow cannula;

said first connecting means comprises a first nut for threadedly engaging threads on the first part on the inflow cannula;

said second connecting means comprises a second nut and a threaded adapter, said adapter having a first threaded portion for threadedly engaging threads on the second part of the inflow cannula and a second threaded portion for threadedly engaging said second nut.

16. The apparatus of claim 15 wherein said first end of said conduit is sandwiched between threads on said first nut and the threads on the first part of the inflow cannula.

17. The apparatus of claim 15 wherein said second end of said conduit is sandwiched between threads on said second nut and threads on said adapter.

18. The apparatus of claim 15 wherein said first connecting means comprises an adhesive for bonding said first end of said conduit to the first part on the inflow cannula.

19. The apparatus of claim 18 wherein said second connecting means comprises a rotating seal disposed at said second end of said conduit, said rotating seal for sealingly engaging the second part of the inflow cannula and allowing rotation of the second part relative to said rotating seal.

20. The apparatus of claim 15 further comprising means for occluding blood flow through said conduit.

21. An apparatus for use with an inflow cannula for directing blood flow from a heart to a ventricular assist device (VAD), the inflow cannula having a first part for connecting with a ventricle of the heart and a second part for connecting with the VAD, said apparatus comprising:

a conduit made of a flexible material, said conduit having oppositely disposed threaded first and second ends and a main body portion intermediate said ends, said main body portion being movable between a radially collapsed closed condition in which blood flow through said conduit is blocked and a radially expanded open condition in which blood flow through said conduit is not blocked;

a first nut circumferentially disposed about said first end of said conduit for connecting said first end to the first part of the inflow cannula;

a threaded adapter for connecting to the second part of the inflow cannula; and a second nut circumferentially disposed about said second end of said conduit and connecting said second end to said adapter.

22. The apparatus of claim 21 wherein said main body portion has an accordion-like configuration to allow for relative axial and radial movement of said ends.

23. The apparatus of claim 21 which said adapter has first and second threaded portions, said first threaded portion for threadedly engaging the second part of the inflow cannula, said second threaded portion threadedly engaging said second nut.

24. The apparatus of claim 23 wherein said first end of said conduit is sandwiched between threads on said first nut and threads on the first part of the inflow cannula.

25. The apparatus of claim 23 wherein said second end of said conduit is sandwiched between threads on said second nut and said second threaded portion of said adapter.

26. The apparatus of claim 21 further comprising means for occluding blood flow through said conduit.

27. The apparatus of claim 26 wherein said means for occluding blood flow comprises a surgical clamp.

28. The apparatus of claim 26 wherein said means for occluding blood flow comprises a threaded plug that is connected to said second nut.

29. The apparatus of claim 21 further comprising means for preventing relative axial and radial movement of said ends of said conduit away from each other.

30. An apparatus for use with an inflow cannula for directing blood flow from a heart to a ventricular assist device (VAD), the inflow cannula having a first threaded part for connecting with a ventricle of the heart and a second threaded part for connecting with the VAD, said apparatus comprising:

a conduit having oppositely disposed threaded first and second ends and a main body portion intermediate said ends, said main body portion having a resiliently flexible section that is compressible to a closed condition in which blood flow through said conduit is blocked;

a first nut circumferentially disposed about said first end of said conduit for connecting said first end to the first threaded part of the inflow cannula;

a threaded adapter for connecting to the second threaded part of the inflow cannula; and a second nut circumferentially disposed about said second end of said conduit and connecting said second end to said adapter.

31. The apparatus of claim 30 wherein said first end of said conduit is sandwiched between threads on said first nut and threads on the first threaded part of the inflow cannula.

32. The apparatus of claim 30 wherein said second end of said conduit is sandwiched between threads on said second nut and threads on said adapter.

33. The apparatus of claim 32 further comprising means for preventing relative axial and radial movement of said ends of said conduit away from each other.

34. An apparatus for use with an inflow cannula of a ventricular assist device (VAD), the inflow cannula having a first part for connecting with a ventricle of a heart and a second part for connecting with the VAD, said apparatus comprising:

a conduit made of a flexible material, said conduit having oppositely disposed first and second ends and a main body portion intermediate said ends, said main body portion having an accordion-like configuration to allow for relative axial and radial movement of said ends;

first connecting means for connecting said first end of said conduit to the first part of the inflow cannula;

second connecting means for connecting said second end of said conduit to the second part of the inflow cannula; and means for occluding blood flow through said main body portion of said conduit;

said first connecting means comprises a first nut for threadedly engaging threads on the first part on the inflow cannula;

said second connecting means comprises a second nut and a threaded adapter, said adapter having a first threaded portion for threadedly engaging threads on the second part of the inflow cannula and a second threaded portion for threadedly engaging said second nut.

35. The apparatus of claim 34 wherein said means for occluding blood flow comprises a surgical clamp.

36. The apparatus of claim 34 wherein said means for occluding blood flow comprises a threaded plug that is connected to said second connecting means.

37. The apparatus of claim 34 further comprising means for preventing relative axial and radial movement of said ends of said conduit away from each other.

38. An apparatus for use with an inflow cannula for directing blood flow from a heart to a ventricular assist device (VAD), the inflow cannula having a first part for connecting with a ventricle of a heart and a second part for connecting with the VAD, said apparatus comprising:

a conduit made of a flexible material, said conduit having oppositely disposed first and second ends and a main body portion intermediate said ends, said main body portion having an accordion-like configuration to allow for relative axial and radial movement of said ends;

a first nut circumferentially disposed about said first end of said conduit for connecting said first end to the first part of the inflow cannula;

an adapter for connecting to the second part of the inflow cannula;

a second nut circumferentially disposed about said second end of said conduit and connecting said second end to said adapter; and means for occluding blood flow through said main body portion of said conduit.

39. The apparatus of claim 38 wherein said means for occluding blood flow comprises a surgical clamp.

40. The apparatus of claim 38 wherein said means for occluding blood flow comprises a threaded plug that is connected to said second connecting means.

41. The apparatus of claim 38 further comprising means for preventing relative axial and radial movement of said ends of said conduit away from each other.

42. The apparatus of claim 38 which said adapter has first and second threaded portions, said first threaded portion for threadedly engaging the second part of the inflow cannula, said second threaded portion threadedly engaging said second nut.

43. The apparatus of claim 42 wherein said first end of said conduit is sandwiched between threads on said first nut and the threads on the first part of the inflow cannula.

44. The apparatus of claim 43 wherein said second end of said conduit is sandwiched between threads on said second nut and said second threaded portion of said adapter.

45. An apparatus for use with a ventricular assist device (VAD), said apparatus comprising:

an inflow cannula having a first part for connecting with a ventricle of a heart and a second part for connecting with the VAD;

a conduit made of a flexible material, said conduit having oppositely disposed first and second ends and a main body portion intermediate said ends, said main body portion having an accordion-like configuration to allow for relative axial and radial movement of said ends;

first connecting means for connecting said first end of said conduit to said first part of said inflow cannula;

second connecting means for connecting said second end of said conduit to said second part of said inflow cannula; and means for occluding blood flow through said inflow cannula;

said first connecting means comprises a first nut for threadedly engaging threads on the first part on the inflow cannula;

said second connecting means comprises a second nut and a threaded adapter, said adapter having a first threaded portion for threadedly engaging threads on said second cart of said inflow cannula and a second threaded portion for threadedly engaging said second nut.

46. The apparatus of claim 45 wherein said means for occluding blood flow comprises a surgical clamp.

47. The apparatus of claim 45 wherein said means for occluding blood flow comprises a threaded plug that is connected to said second connecting means.

48. The apparatus of claim 45 further comprising means for preventing relative axial and radial movement of said ends of said conduit away from each other.

49. The apparatus of claim 45 wherein said first connecting means comprises an adhesive for bonding said first end of said conduit to the first part on the inflow cannula.

50. The apparatus of claim 49 wherein said second connecting means comprises a rotating seal disposed at said second end of said conduit, said rotating seal for sealingly engaging the second part of the inflow cannula and allowing rotation of the second part relative to said rotating seal.

51. An apparatus for use with a ventricular assist device (VAD), said apparatus comprising:

an inflow cannula having a first part for connecting with a ventricle of a heart and a second part for connecting with the VAD;

a conduit made of a flexible material, said conduit having oppositely disposed first and second ends and a main body portion intermediate said ends, said main body portion having an accordion-like configuration to allow for relative axial and radial movement of said ends;

first connecting means for connecting said first end of said conduit to said first part of said inflow cannula;

second connecting means for connecting said second end of said conduit to said second part of said inflow cannula; and means for occluding blood flow through said inflow cannula comprising an inflatable balloon.

52. The apparatus of claim 51 wherein said first part of said inflow cannula includes an opening and a removable screw positionable in said opening, said balloon being insertable into said inflow cannula through said opening when said screw is removed.

* * * * *

UNITED STATES PATENT AND TRADEMARK OFFICE

CERTIFICATE OF CORRECTION

PATENT NO. : 6,802,806 B2
DATED : October 12, 2004
INVENTOR(S) : Patrick McCarthy et al.

It is certified that error appears in the above-identified patent and that said Letters Patent is hereby corrected as shown below:

Column 13,
Line 22, after "second" change "cart" to -- part --.
Line 58, after "first" change "cart" to -- part --.

Column 15,
Line 42, after "claim" change "32" to -- 30 --.

Signed and Sealed this

Twenty-sixth Day of April, 2005

JON W. DUDAS
*Director of the United States Patent and Trademark Office*